United States Patent
Conboy et al.

(10) Patent No.: US 9,758,763 B2
(45) Date of Patent: Sep. 12, 2017

(54) METHODS AND COMPOSITIONS FOR SOMATIC CELL PROLIFERATION AND VIABILITY

(71) Applicant: The Regents of the University of California, Oakland, CA (US)

(72) Inventors: Irina M. Conboy, El Sobrante, CA (US); Michael J. Conboy, El Sobrante, CA (US); Hanadie Yousef, Berkeley, CA (US); David V. Schaffer, Danville, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/288,117

(22) Filed: May 27, 2014

(65) Prior Publication Data

US 2014/0356947 A1 Dec. 4, 2014

Related U.S. Application Data

(60) Provisional application No. 61/828,543, filed on May 29, 2013.

(51) Int. Cl.
*C12N 5/00* (2006.01)
*C12N 5/0793* (2010.01)
*C12N 5/077* (2010.01)

(52) U.S. Cl.
CPC ......... *C12N 5/0619* (2013.01); *C12N 5/0659* (2013.01); *C12N 2501/91* (2013.01); *C12N 2502/02* (2013.01)

(58) Field of Classification Search
None
See application file for complete search history.

(56) References Cited

U.S. PATENT DOCUMENTS

| | | | |
|---|---|---|---|
| 5,061,620 A | 10/1991 | Tsukamoto et al. | |
| 5,843,780 A | 12/1998 | Thomson | |
| 6,200,806 B1 | 3/2001 | Thomson | |
| 7,029,913 B2 | 4/2006 | Thomson | |
| 7,837,993 B2 | 11/2010 | Conboy et al. | |

OTHER PUBLICATIONS

Conboy et al., Science 302: 1575-1577 (2003).*
Carlson et al., Aging Cell 6: 371-382 (2007).*
Balis and Poplack (1989) "Central nervous system pharmacology of antileukemic drugs" Journal of Pediatric Hematology/Oncology 11(1):74-86.

(Continued)

*Primary Examiner* — Erin M Bowers
(74) *Attorney, Agent, or Firm* — Edward J. Baba; Shweta Chandra; Bozicevic, Field & Francis LLP

(57) ABSTRACT

Methods and compositions for somatic cell proliferation as well as increasing viability of somatic cells are provided. The compositions include heparin binding protein isolated from a medium conditioned by growth of pluripotent stem cells, such as, human embryonic stem cells, human embryonic carcinoma cells. The methods include contacting a somatic cell with a heparin binding protein composition for a sufficient period of time to provide for enhanced proliferation and/or viability of the somatic cell as compared to the absence of the heparin binding protein composition.

13 Claims, 13 Drawing Sheets

(56) References Cited

OTHER PUBLICATIONS

Barghorn et al. (2005) "Globular amyloid β-peptide 1-42 oligomer—a homogenous and stable neuropathological protein in Alzheimer's disease" Journal of Neurochemistry 95(3):834-847.
Bischoff (1990) "Cell cycle commitment of rat muscle satellite cells" The Journal of Cell Biology 111(1):201-207.
Bischoff (1986) "Proliferation of muscle satellite cells on intact myofibers in culture" Developmental Biology 115 (1):129-139.
Buchli and Schwab (2005) "Inhibition of Nogo: a key strategy to increase regeneration, plasticity and functional recovery of the lesioned central nervous system" Annals of Medicine 37(8):556-567.
Carlson and Conboy (2007) "Loss of stem cell regenerative capacity within aged niches" Aging Cell 6(3):371-382.
Chung et al. (2008) "Human Embryonic Stem Cell Lines Generated without Embryo Destruction" Cell Stem Cell 2 (2):113-117.
Conboy and Conboy (2010) "Preparation of adult muscle fiber-associated stem/precursor cells" Methods Mol Biol 621:149-163.
Conboy et al. (2003) "Notch-Mediated Restoration of Regenerative Potential to Aged Muscle" Science 302:1575-1577.
Conboy et al. (2010) "Immuno-analysis and FACS sorting of adult muscle fiber-associated stem/precursor cells" Methods Mol Biol 621:165-173.
Conboy et al. (2011) "Embryonic anti-aging niche" Aging 3(5):555-563.
Conboy and Rando (2002) "The Regulation of Notch Signaling Controls Satellite Cell Activation and Cell Fate Determination in Postnatal Myogenesis" Dev Cell 3:397-409.
Conboy and Rando (2012) "Heterochronic parabiosis for the study of the effects of aging on stem cells and their niches" Cell Cycle 11(12):2260-2267.
Grounds (1998) "Age-associated Changes in the Response of Skeletal Muscle Cells to Exercise and Regeneration" Ann NY Acad Sci 854:78-91.
Jensen et al. (2000) "Quantification of Alzheimer amyloid beta peptides ending at residues 40 and 42 by novel ELISA systems" Mol Med 6(4):291-302.
Kuo et al. (1996) "Water-soluble Ab (N-40, N-42) Oligomers in Normal and Alzheimer Disease Brains" J Biol Chem 271(8):4077-4081.
Ludwig et al. (2006) "Feeder-independent culture of human embryonic stem cells" Nat Methods 3(8):637-646.
Ma et al. (2007) "An experimental test of stroke recovery by implanting a hyaluronic acid hydrogel carrying a Nogo receptor antibody in a rat model" Biomed Mater 2(4):233-240.
Morrison et al. (1997) "Regulatory Mechanisms in Stem Cell Biology" Cell 88(3):287-298.
Morrison et al. (1999) "Prospective Identification, Isolation by Flow Cytometry, and In Vivo Self-Renewal of Multipotent Mammalian Neural Crest Stem Cells" Cell 96:737-749.
Pardridge (2008) "Re-Engineering Biopharmaceuticals for Delivery to Brain with Molecular Trojan Horses" Bioconjugate Chem 19:1327-1338.
Piantino et al. (2006) "An injectable, biodegradable hydrogel for trophic factor delivery enhances axonal rewiring and improves performance after spinal cord injury" Experimental Neurology 201(2):359-367.
Shoichet et al. (2007) "Intrathecal drug delivery strategy is safe and efficacious for localized delivery to the spinal cord" Progress in Brain Research 161:385-392.
Tosi et al. (2008) "Polymeric nanoparticles for the drug delivery to the central nervous system" Expert Opinion on Drug Delivery 5(2):155-174.
Ulbrich et al. (2009) "Transferrin- and transferrin-receptor-antibody-modified nanoparticles enable drug delivery across the blood-brain barrier (BBB)" Eur J Pharm Biopharm 71(2):251-256.
Vyas et al. (2006) "Formulation and Physiological Factors Influencing CNS Delivery upon Intranasal Administration" Crit Rev Ther Drug Carrier Syst 23(4):319-347.
Yu et al. (2009) "Structural characterization of a soluble amyloid β-peptide oligomer" Biochemistry 48(9):1870-1877.
Conboy and Rando (2005) "Aging, stem cells and tissue regeneration: lessons from muscle" Cell Cycle 4(3):407-410.

* cited by examiner

FIGURE 1 (continued)
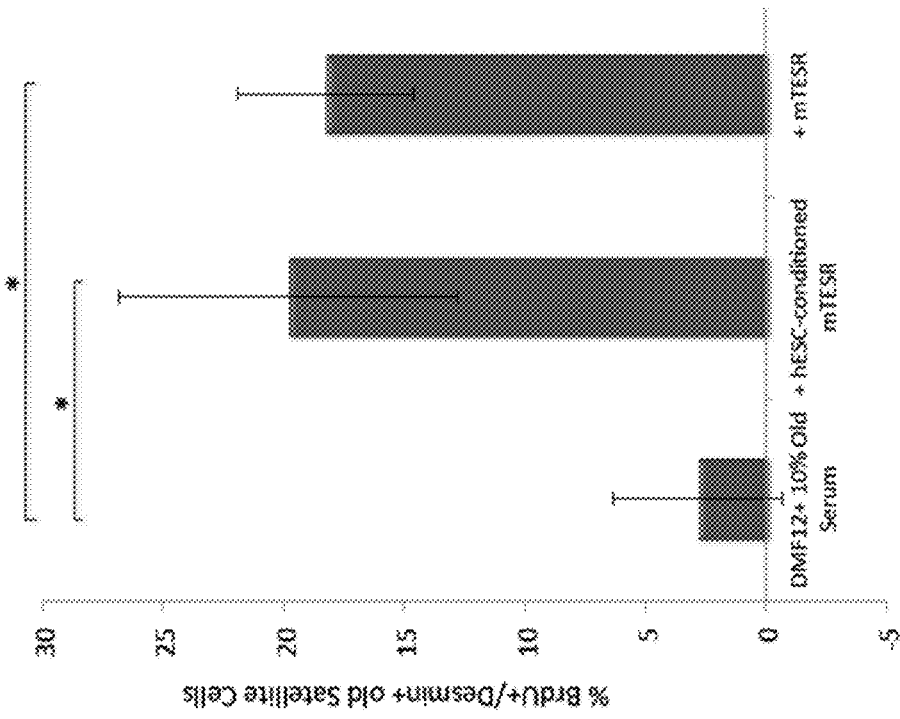
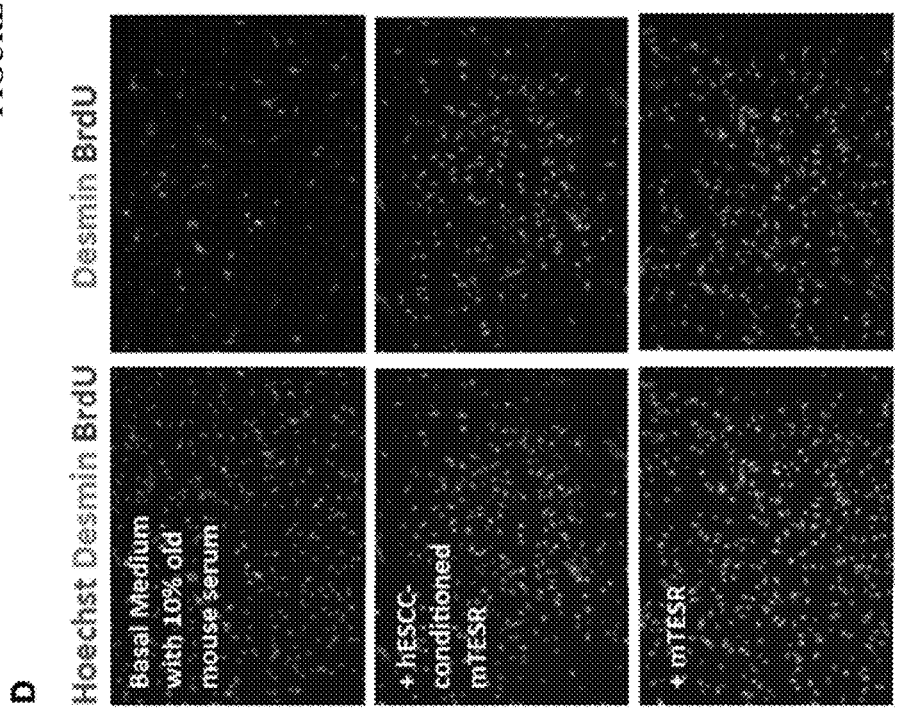

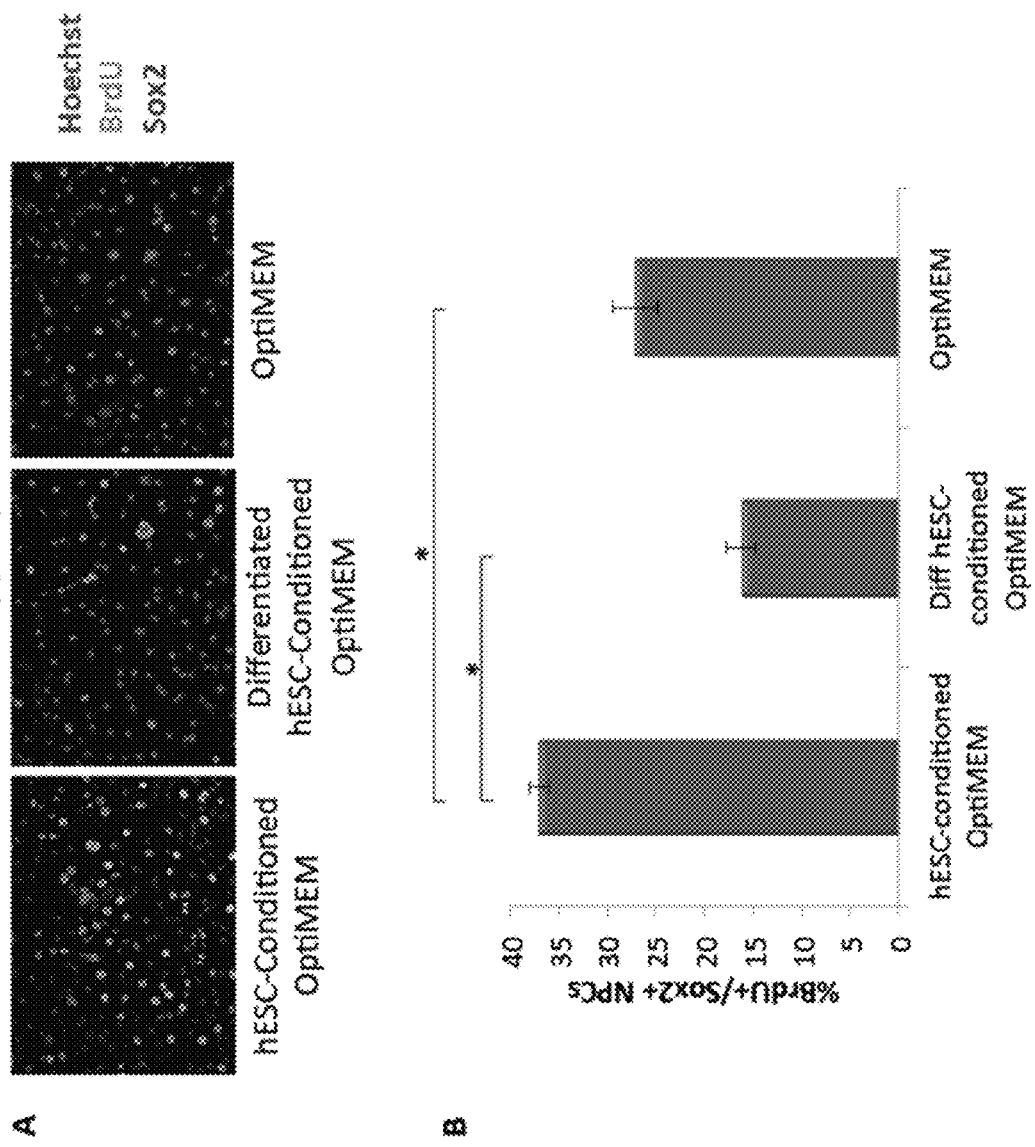

METHODS AND COMPOSITIONS FOR SOMATIC CELL PROLIFERATION AND VIABILITY

CROSS-REFERENCE TO RELATED APPLICATION

Pursuant to 35 U.S.C. §119(e), this application claims priority to the filing date of U.S. Provisional Application No. 61/828,543, filed May 29, 2013, the disclosure of which is incorporated herein by reference.

STATEMENT REGARDING FEDERALLY SPONSORED RESEARCH

This invention was made with government support under Grant No. AG027252 awarded by National Institutes of Health. The government has certain rights in the invention.

INTRODUCTION

Unlike embryonic stem cells, somatic cells have a limited capacity for regeneration. While, embryonic stem cells have generated considerable interest, the stem cells resident in differentiated tissues may also provide an important source of regenerative capacity. These somatic, or adult, stem cells are undifferentiated cells that reside in differentiated tissues, and have the properties of self-renewal and generation of differentiated cell types. The differentiated cell types may include all or some of the specialized cells in the tissue. For example, hematopoietic stem cells give rise to all hematopoietic lineages, but do not seem to give rise to stromal and other cells found in the bone marrow.

Sources of somatic stem cells include bone marrow, blood, the cornea and the retina of the eye, brain, skeletal muscle, dental pulp, liver, skin, the lining of the gastrointestinal tract, and pancreas. Progenitor or precursor cells are similar to stem cells, but are usually considered to be distinct by virtue of lacking the capacity for self-renewal.

Muscle tissue in adult vertebrates regenerates from reserve myoblasts called satellite cells. Satellite cells are distributed throughout muscle tissue and are mitotically quiescent in the absence of injury or disease. Following recovery from damage due to injury or disease or in response to stimuli for growth or hypertrophy, satellite cells reenter the cell cycle, proliferate and enter existing muscle fibers or undergo differentiation into multinucleated myotubes, which form new muscle fiber. The myoblasts ultimately yield replacement muscle fibers or fuse into existing muscle fibers, thereby increasing fiber girth.

Although, stem cells and progenitor cells present in organs of an adult organism can proliferate and lead to generation of new somatic cells to replace older, injured, diseased, dying, or dead somatic cells, the stem cells and progenitor cells may lose this capacity due to a number of causes.

With aging and in certain disease conditions, old differentiated cells lose their functionality or die, while stem and progenitor cells dedicated to generating new differentiated cells lose their regenerative capacity.

With explantation and in vitro culture, adult stem and progenitor cells lose stem cell function and proliferative capacity, and suffer high mortality when reintroduced in vivo.

As such, there is an interest in methods and compositions that may increase proliferation of somatic cells and/or increase their viability.

SUMMARY

Methods and compositions for somatic cell proliferation as well as increasing viability of somatic cells are provided. The compositions include heparin binding protein(s) isolated from a medium conditioned by growth of human embryonic stem cells. The methods include contacting a somatic cell with a heparin binding protein composition for a sufficient period of time to provide for enhanced proliferation and/or viability of the somatic cell as compared to the absence of the heparin binding protein composition.

In certain embodiments, a method for enhancing proliferation of a somatic cell is provided. The method may include contacting a somatic cell with heparin binding protein composition, wherein the composition includes heparin binding protein isolated from a medium conditioned by growth of human embryonic stem cells, where the contacting is for a period of time sufficient to provide for enhanced proliferation of the somatic cell compared to the absence of the heparin binding protein composition.

In certain cases, the somatic cell may be a cell of an aged subject. In certain cases, the somatic cell, e.g., a cell of an aged subject, may be an injured cell. The injury may be caused by a disease. In certain cases, the somatic cell, e.g., a cell of an aged subject, may be a diseased cell, or an explanted adult stem cell or an explanted progenitor cell.

In certain embodiments, the somatic cell may be a muscle cell, e.g., a skeletal muscle cell, a myoblast, a satellite cell, or an activated satellite cell. The muscle cell may be a cell of an aged subject, an injured cell, a cell injured due to disease, a diseased cell, a cell of an aged subject that is injured, e.g., due to a disease, or is a diseased cell, or an explanted adult stem cell or an explanted progenitor cell.

In certain embodiments, the somatic cell may be a neural cell, e.g., neural stem cell, neural progenitor cells, or a neuron. The neural cell may be a cell of an aged subject, an injured cell, a cell injured due to disease, a diseased cell, a cell of an aged subject that is injured, e.g., due to a disease, or is a diseased cell, or an explanted adult stem cell or an explanted progenitor cell.

In certain embodiments, the heparin binding protein composition may include a plurality of heparin binding proteins isolated from a medium conditioned by growth of human embryonic stem cells.

Also provided herein, is use of a heparin binding protein composition, wherein the composition includes heparin binding protein isolated from a medium conditioned by growth of human embryonic stem cells, for enhancing proliferation of a somatic cell by contacting the somatic cell with the heparin binding protein composition for a period of time sufficient to provide for enhanced proliferation of the somatic cell as compared to the absence of the heparin binding protein composition.

The present disclosure also provides a method of increasing viability of a neuron. The method may include contacting the neuron with heparin binding protein composition, wherein the composition includes heparin binding protein isolated from a medium conditioned by growth of human embryonic stem cells, wherein the contacting is for a period of time sufficient to provide for increasing viability of the neuron as compared to the absence of the heparin binding protein composition.

The neuron may be a cortical neuron, for example, a glutamatergic neuron.

In certain cases, the neuron may be exposed to a toxin, such as, an amyloid beta globulomer.

Also provided herein, is use of a heparin binding protein composition, wherein the composition includes heparin binding protein isolated from a medium conditioned by growth of human embryonic stem cells, for increasing viability of a neuron by contacting the neuron with the heparin binding protein composition for a period of time sufficient to provide for increasing viability of the neuron as compared to the absence of the heparin binding protein composition.

Methods are also provided for screening of other agents that can improve somatic cell proliferation and/or increase viability of somatic cells in the presence of heparin binding protein composition.

Muscle stem cell isolated from young and old mice were cultured for 24 hours and then immunostained for myogenic markers Pax7 and Myf-5. ~95% of isolated young and old satellite cells expressed these myogenic markers, demonstrating high and age-independent purity.

Figure 7:
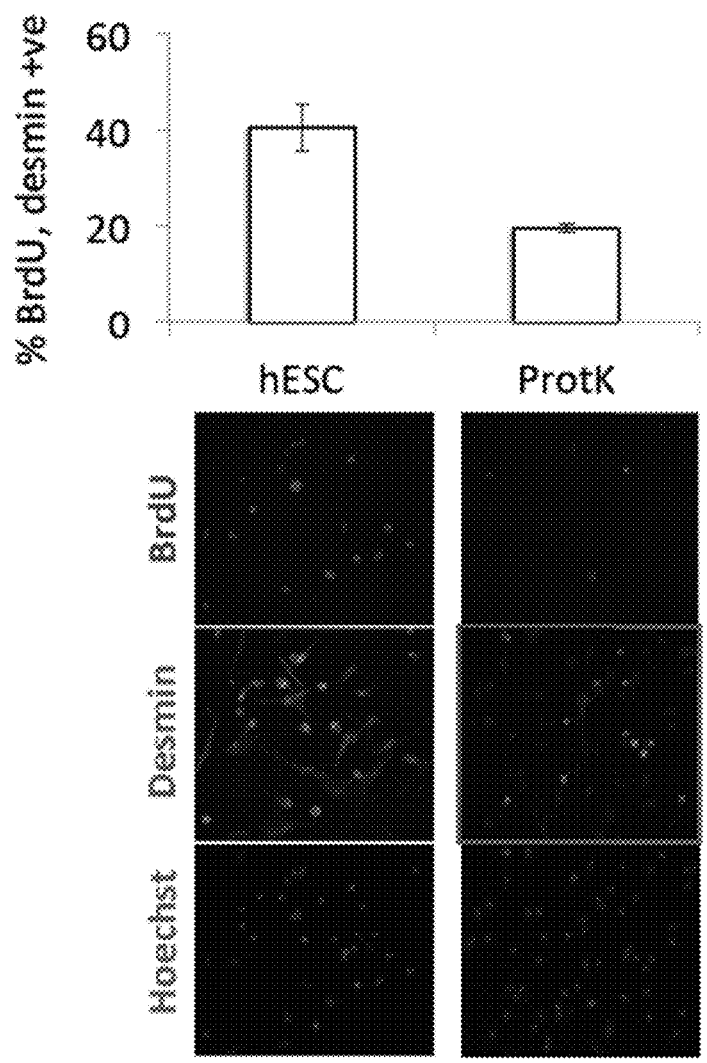

FIG. 7. Proteinase K treatment abolishes proliferative hESC factors. Old injury-activated satellite cells with associated myofibers were cultured overnight in 50% Opti-MEM with 10% old serum and 50% hESC conditioned Opti-MEM that was treated with pre-washed Proteinase K agarose beads (Sigma-Aldrich), for 1 hour at 37 C followed by bead removal, or mock-treated hESC conditioned Opti-MEM. Cells received a 2 hour BrdU pulse to label proliferating cells before cell fixation. Immunofluorescence was performed for Desmin (green) and BrdU (red), with Hoechst (blue) labeling all cell nuclei. Proliferating, desmin+ve cells were quantified by imaging and scoring multiple random microscopic fields of each condition. Results are displayed as the mean percent of BrdU+,Desmin+ proliferating satellite cell cells +/−SEM, p<0.005, n=3 replicate experiments.

Figure 8:
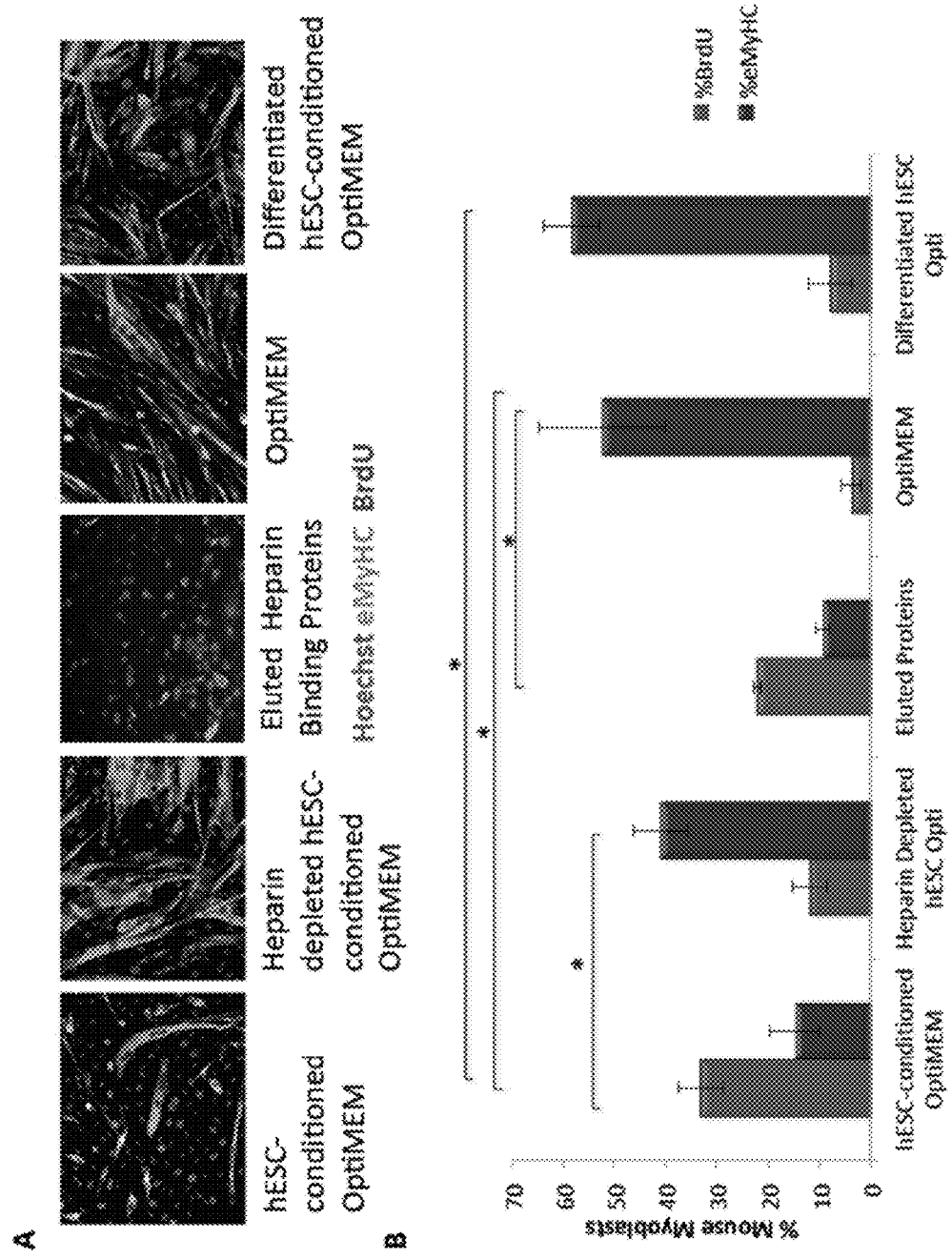
Figure 8:
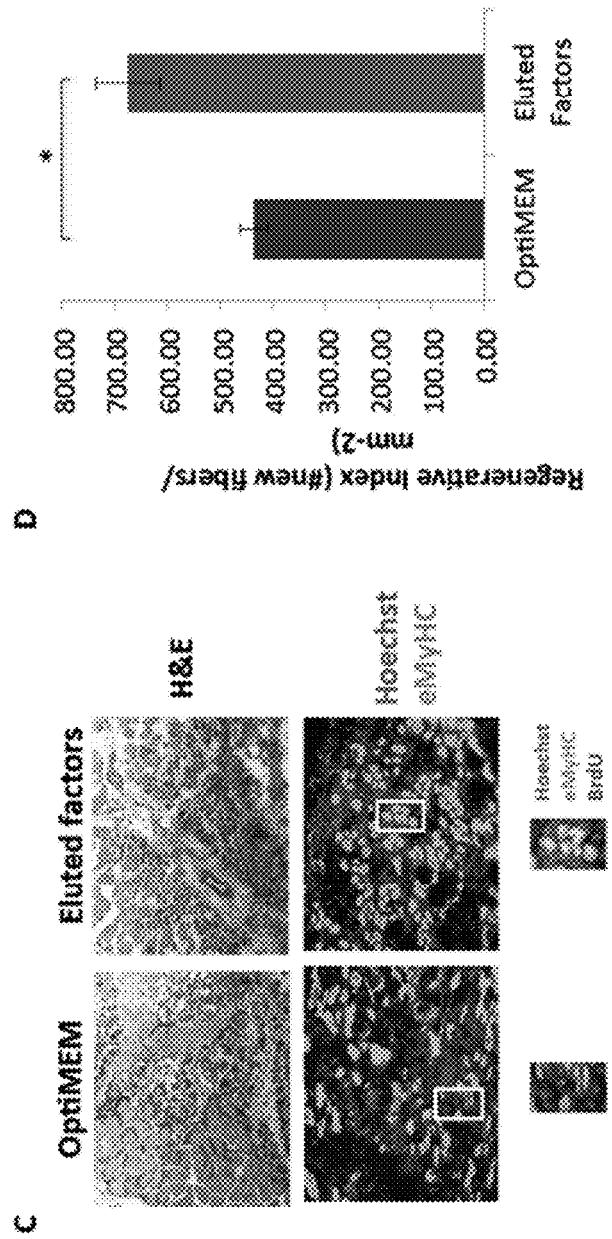

FIG. 8. Pro-regenerative Embryonic Factors Contain Heparin Binding Domains. (A) Primary Mouse Myoblasts were cultured for 24 hours in 50% fusion/differentiation medium+50% of the specified medium. A 2 hour BrdU pulse was performed before cell fixation to label proliferating cells. Immunofluorescence was performed for eMyHC (green) and BrdU (red), with Hoechst (blue) labeling all nuclei. Representative images are shown. (B) Proliferation and differentiation of fusion-competent myoblasts were quantified by cell scoring in 25-100 random fields of each condition using an automated imager and MetaXpress cell scoring software. Results are displayed as the mean percent of BrdU+ or eMyHC+ proliferating or differentiating cells +/−SD, respectively. N=6*P<3×10$^{-45}$ for hESC-conditioned Opti-MEM compared to differentiated hESC-conditioned Opti-MEM, and hESC-conditioned Opti-MEM compared to Opti-MEM. *P<0.005 for hESC-conditioned Opti-MEM compared to heparin depleted hESC-conditioned Opti-MEM, and hESC-conditioned Opti-MEM compared to differentiated hESC-conditioned OptiMEM. *P<5×10$^{-7}$ for hESC-conditioned Opti-MEM compared to Opti-MEM, and Eluted Proteins compared to Opti-MEM. (C) Old Tibialis Anterior muscles were injured with cardiotoxin (see Methods). Heparin bound and eluted protein or vehicle control (Opti-MEM) were injected into sites of injury on Day 0 and Day 2. BrdU was injected (intraperitoneal) at 3 days post injury to label proliferating, fusion-competent myoblasts. Animals were sacrificed and muscle was collected 5 days post injury. Cryosections (10 μm) were analyzed by hematoxylin/eosin (H&E) staining and immunostaining for embryonic myosin heavy chain (eMyHC, shown in green) and BrdU incorporation (shown in red). Hoechst stains nuclei (blue). As shown by representative images, the regenerative outcome of old muscle given eluted factors was significantly improved as compared to old muscle given Opti-MEM vehicle control, based on significantly diminished scar tissue formation, larger and more dense de novo myofibers and an increase in the numbers of eMyHC+ myofibers with centrally-located BrdU+ nuclei that replaced the damaged tissue. (D) Regeneration of old mouse Tibialis Anterior 5 days post injury, that received eluted factors or vehicle, was quantified from muscle sections, and is presented as the number of newly regenerated myofibers per square millimeter of injury site. Error bars indicate SD, n=3 mice per group. *P<0.02 between old given eluted factors and old given vehicle control.

Figure 9:
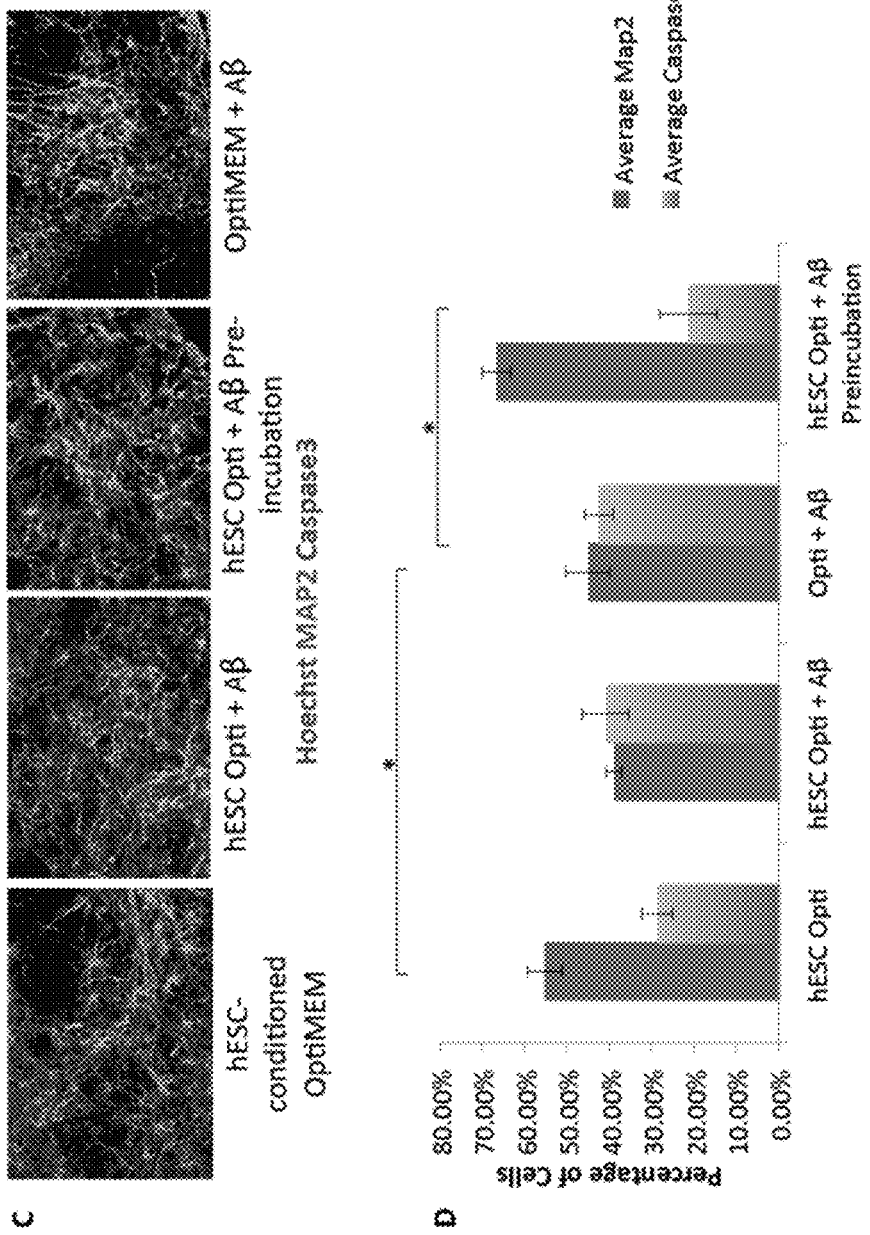

FIG. 9. hESC-secreted Factors Enhance NPC Proliferation and are Neuroprotective. (A) Rat Neural Progenitor Cells (rNPCs) were cultured overnight in 50% differentiation medium (DMF12+N2) and 50% specified medium followed by a 4 hour BrdU pulse to label proliferating cells prior to fixation. Immunofluorescence was performed for Sox2 (red) and BrdU (green), with Hoechst (blue) labeling cell nuclei. Representative images are shown. (B) Quantification of BrdU+/Sox2+ proliferating cells was performed by cell scoring in 100 random fields of each condition using an automated imager and MetaXpress cell scoring software. Results are displayed as the mean percent of BrdU+/Sox2+ proliferating cells +/−SD; N=4, *P<2×10$^{-15}$ for rNPCs incubated in hESC-conditioned Opti-MEM as compared to rNPCs incubated in differentiated hESC-conditioned Opti-MEM, and *P<0.0002 for rNPCs incubated in hESC-conditioned Opti-MEM as compared to rNPCs incubated in Opti-MEM. (C) Pre-incubation of Aβ globulomers with hESC-conditioned Opti-MEM before incubation with mature cortical neurons prevents neuron cell death and exhibits a neurotrophic effect, as shown via decreased immunofluorescence staining of cleaved caspase3 (red) and increased Map2+ (green) neurons. Hoechst (blue) labels all nuclei. Representative images are shown. (D) Total number of Map2+ neurons and the amount of apoptosis was quantified by cell scoring of random fields taken by an automated imager of each condition in the above assay performed in replicates. Results are displayed as the mean percent of caspase+ or Map2+ (C) proliferating or differentiating cells +/−SD, respectively. N=4, *P<0.02 for Map2+ cortical neurons treated with Aβ globulomers preincubated in hESC-conditioned Opti-MEM, as compared to treatment with Aβ globulomers in OptiMEM, and *P<0.05 for the level of caspase3 in cortical neurons treated with Aβ globulomers preincubated in hESC-conditioned Opti-MEM, as compared to treatment with Aβ globulomers in Opti-MEM.

DEFINITIONS

By "embryonic stem cell" or "ES cell" it is meant a cell that a) can self-renew, b) can differentiate to produce all types of cells in an organism, and c) is derived from a developing organism or is an established ES cell line which was derived from a developing organism. ES cell may be derived from the inner cell mass of the blastula of a developing organism. ES cell may be derived from a blastomere generated by single blastomere biopsy (SBB) involving removal of a single blastomere from the eight cell stage of a developing organism. In general, SBB provides a non-destructive alternative to inner cell mass isolation. SBB and generation of hES cells from the biopsied blastomere is described in Cell Stem Cell, 2008 Feb. 7; 2(2):113-7. ES cells can be cultured over a long period of time while maintaining the ability to differentiate into all types of cells in an organism. In culture, ES cells typically grow as flat colonies with large nucleo-cytoplasmic ratios, defined borders and prominent nuclei. In addition, ES cells express SSEA-3, SSEA-4, TRA-1-60, TRA-1-81, and Alkaline Phosphatase, but not SSEA-1. Examples of methods of generating and characterizing ES cells may be found in, for example, U.S. Pat. Nos. 7,029,913, 5,843,780, and 6,200,806, the disclosures of which are incorporated herein by reference.

By "somatic cell" it is meant any cell of an organism that, in the absence of experimental manipulation, does not ordinarily give rise to all types of cells in an organism. In other words, somatic cells are cells that have differentiated sufficiently that they will not naturally generate cells of all three germ layers of the body, i.e., ectoderm, mesoderm and endoderm. For example, somatic cells would include both neurons and neural progenitors, the latter of which may be able to self-renew and naturally give rise to all or some cell types of the central nervous system but cannot give rise to cells of the mesoderm or endoderm lineages.

By "pluripotent stem cell" or "pluripotent cell" it is meant a cell that has the ability under appropriate conditions of producing progeny of several different cell types that are derivatives of all of the three germinal layers (endoderm, mesoderm, and ectoderm) Pluripotent stem cells are capable of forming teratomas. Examples of pluripotent stem cells are embryonic stem (ES) cells, embryonic germ stem (EG) cells, embryonic Carcinoma (EC) Cells, induced pluripotent stem (iPS) cells, and adult stem cells. PS cells may be from any organism of interest, including, primate, e.g., human; canine; feline; murine; equine; porcine; avian; camel; bovine; ovine, and so on.

The terms "treatment", "treating" and the like are used herein to generally mean obtaining a desired pharmacologic and/or physiological effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual", "subject", "host", and "patient" are used interchangeably herein and refer to any mammalian subject for whom diagnosis, treatment, or therapy is desired, e.g., humans.

By "endoderm" it is meant the germ layer formed during animal embryogenesis that gives rise to the gastrointestinal tract, respiratory tract, endocrine glands and organs, certain structures of the auditory system, and certain structures of the urinary system.

By "mesoderm" it is meant the germ layer formed during animal embryogenesis that gives rise to muscles, cartilage, bones, dermis, the reproductive system, adipose tissue, connective tissues of the gut, peritoneum, certain structures of the urinary system, mesothelium, notochord, and spleen.

By "ectoderm" it is meant the germ layer formed during animal embryogenesis that gives rise to the nervous system, tooth enamel, epidermis, hair, nails, and linings of mucosal tissues.

The term "medium" in context of cell culture or the phrase "cell culture medium" or "cell medium" or "growth medium" refer to a cellular growth medium suitable for culturing of human ES cells. Examples of cell culture medium include Minimum Essential Medium (MEM), Eagle's Medium, Dulbecco's Modified Eagle Medium (DMEM), Dulbecco's Modified Eagle Medium: Nutrient Mixture F-12 (DMEM/F12), F10 Nutrient Mixture, Ham's F10 Nutrient Mix, Ham's F12 Nutrient Mixture, Medium 199, RPMI, RPMI 1640, reduced serum medium, basal medium (BME), DMEM/F12 (1:1), and the like, and combinations thereof. The medium or cell culture medium may be modified by adding one or more additives. Additives may include serum, such as, fetal bovine serum and/or serum replacement agents, such as, B27, N2, KSR, and combinations thereof.

The term "enriched" used herein in the context of heparin binding protein(s) means that the fraction of heparin binding protein(s) is increased by at least 10% over the fraction of other proteins in the culture medium.

A "pharmaceutically acceptable carrier" means carrier that is useful in preparing a pharmaceutical composition that is generally safe, non-toxic and neither biologically nor otherwise undesirable, and include carriers that are acceptable for veterinary use as well as human pharmaceutical use. A pharmaceutically acceptable carrier as used in the specification includes both one and more than one such carrier.

As used herein, a "pharmaceutical composition" is meant to encompass a composition suitable for administration to a subject, such as a mammal, especially a human. A "pharmaceutical composition" may be sterile and free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration.

As used herein, "marker" refers to any molecule that can be measured or detected. For example, a marker can include, without limitations, a nucleic acid, such as, a transcript of a gene, a polypeptide product of a gene, a glycoprotein, a carbohydrate, a glycolipid, a lipid, a lipoprotein, a carbohydrate, or a small molecule (for example, a molecule having a molecular weight of less than 10,000 amu).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Methods and compositions for somatic cell proliferation as well as increasing viability of somatic cells are provided. The compositions include heparin binding protein isolated from a medium conditioned by growth of human embryonic stem cells, or embryonic carcinoma cells. The methods include contacting a somatic cell with a heparin binding protein composition for a sufficient period of time to provide for enhanced proliferation and/or viability of the somatic cell as compared to the absence of the heparin binding protein composition.

Methods are also provided for screening of other agents that can improve somatic cell proliferation and/or increase viability of somatic cells in the presence of heparin binding protein composition.

The methods and compositions are described in detail below.

Methods For Enhancing Somatic Cell Proliferation And/Or Viability

As noted above, in certain embodiments, a method for enhancing proliferation of a somatic cell is provided. The method may include contacting a somatic cell with heparin binding protein composition, wherein the composition includes heparin binding protein isolated from a medium conditioned by growth of human embryonic stem cells, or embryonic carcinoma cells, where the contacting is for a period of time sufficient to provide for enhanced proliferation of the somatic cell compared to the absence of the heparin binding protein composition.

The present disclosure also provides a method of increasing viability of a somatic cell. The method may include contacting the somatic cell with heparin binding protein composition, wherein the composition includes heparin binding protein isolated from a medium conditioned by growth of human embryonic stem cells, or embryonic carcinoma cells, wherein the contacting is for a period of time sufficient to provide for increasing viability of the somatic cell as compared to the absence of the heparin binding protein composition.

Any somatic cell may be used in the present methods, including but not limited to, stem cell, progenitor cell, muscle cell, myoblast, satellite cell, neuron, blood cell, and the like.

The term stem cell is used herein to refer to a mammalian cell that has the ability both to self-renew, and to generate differentiated progeny (see Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting. In certain cases, the somatic cell may be an explanted stem cell or progenitor cell. In certain cases, the explanted stem cell or progenitor cell may have been subjected to culturing for a prolonged duration of time, such as, 1 day to 10 years or more, such as, 1 day, 3 days, 7 days, 2 weeks, 5 weeks, 10 weeks, 3 months, 10 months, 1 year, 3 years, 5 years, 10 years, or more.

Stem cells may be characterized by both the presence of certain markers and the absence of certain markers. These markers may be detected using a number of methods that may depend on the nature of the marker. In some embodiments, the marker may be associated with specific epitopes which are identified by antibodies. Stem cells may also be identified by functional assays both in vitro and in vivo, particularly assays relating to the ability of stem cells to give rise to multiple differentiated progeny.

Stem cells of interest include muscle satellite cells; hematopoietic stem cells and progenitor cells derived therefrom (U.S. Pat. No. 5,061,620); neural stem cells (see Morrison et al. (1999) Cell 96:737-749); mesenchymal stem cells; mesodermal stem cells; liver stem cells, etc.

The somatic cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human.

In certain embodiments, the somatic cell is a muscle cell. The term muscle cell as used herein refers to any cell that contributes to muscle tissue. Myoblasts, satellite cells, myotubes, and myofibrils are all included in the term "muscle cells". Muscle cell includes skeletal, cardiac and smooth muscle cells.

Activation of satellite cells in muscle tissue can result in the production of new muscle cells in a subject. Muscle regeneration as used herein refers to the process by which new muscle fibers form from muscle stem cells, such as, satellite cells and myoblasts.

In certain embodiments, a method for regeneration of skeletal muscle cell is provided. The method may include contacting a skeletal muscle cell with heparin binding protein composition, wherein the composition includes heparin binding protein isolated from a medium conditioned by growth of human embryonic stem cells, where the contacting is for a period of time sufficient to provide for regeneration of the skeletal muscle cell compared to the absence of the heparin binding protein composition.

In certain embodiments, the skeletal muscle cell may be in a muscle tissue. In certain embodiments, the muscle tissue may include satellite cells. In certain cases, the muscle tissue may be injured resulting in activation of the satellite cells.

In certain cases, the method may include contacting an injured muscles tissue with heparin binding protein composition, wherein the injured muscles tissue includes activated satellite cells, wherein the composition includes heparin binding protein isolated from a medium conditioned by growth of human embryonic stem cells, where the contacting is for a period of time sufficient to provide for proliferation of the activated satellite cells and result in enhanced regeneration of muscle cells in the injured skeletal muscle tissue as compared to the absence of the heparin binding protein composition.

In certain cases, the injured muscle tissue may be of an aged subject. As used herein, the term aged refers to the effects or the characteristics of increasing age, particularly with respect to the diminished ability of somatic tissues to regenerate in response to damage, disease, and normal use. One measure of aging is evidenced by the inability of the organism to provide suitable signals for the activation of somatic stem cells. Examples of such signals are provided in U.S. Pat. No. 7,837,993. Such signals include soluble factors that may be empirically measured, e.g., by functional assay such as the ability of soluble factors in the patient blood to induce stem cell activation in response to tissue damage; or by the ability to induce expression of Notch ligands, by binding assays such as ELISA, RIA, with binding agents specific for Notch ligands; or by the ability to increase the levels of activated Notch, with Western analysis for activated, truncated Notch.

Aging may be also be defined in terms of general physiological characteristics. The rate of aging is very species specific, where a human may be aged at about 50 years; and a rodent at about 2 years. In general terms, a natural progressive decline in body systems starts in early adulthood, but it becomes most evident several decades later. One arbitrary way to define old age more precisely in humans is to say that it begins at conventional retirement age, around about 60, around about 65 years of age. Another definition sets parameters for aging coincident with the loss of reproductive ability, which is around about age 45, more usually around about 50 in humans, but will, however, vary with the individual.

In certain embodiments, the present methods may result in an increase in the number of new skeletal muscle fibers by at least 1%, by at least 5%, by at least 10%, by at least 20%, by at least 30%, by at least 40%, or by at least 50%. The growth of muscle may occur by the increase in the fiber size and/or by increasing the number of fibers. The growth of muscle may be measured by an increase in wet weight, an increase in protein content, an increase in the number of muscle fibers, an increase in muscle fiber diameter, etc. An increase in growth of a muscle fiber can be defined as an increase in the diameter where the diameter is defined as the minor axis of ellipsis of the cross section.

Muscle regeneration may also be monitored by the mitotic index of muscle. For example, cells may be exposed to a labeling agent for a time equivalent to two doubling times. The mitotic index is the fraction of cells in the culture which have labeled nuclei when grown in the presence of a tracer which only incorporates during S phase (e.g., BrdU) and the doubling time is defined as the average S time required for the number of cells in the culture to increase by a factor of two. Productive muscle regeneration may be also monitored by an increase in muscle strength and agility and other measurements of muscle function.

In addition to skeletal muscle regeneration, the regeneration of cardiac muscle in an aged subject is of interest. For example, following an event such as myocardial infarction; surgery, catheter insertion, atherosclerosis, and the like, cardiac muscle can be damaged. Such damage is not easily repaired in elderly patients, resulting in a loss of function. Administration of a heparin binding protein composition, as disclosed herein, following such incidents of muscle damage can increase regeneration of the damaged tissues. The heparin binding protein composition may be administered systemically, or using a stent, catheter, implant, and the like that increase the local concentration of the heparin binding protein composition.

In certain embodiments, the contacting may include administering the heparin-binding protein composition to a subject having or at risk of developing an aging related condition. A number of conditions relevant to aged populations are characterized by an inability to regenerate tissues. All aged organs and tissues undergo a loss of regeneration and maintenance with age, thus this method is applicable to the aged organ systems in general, including muscle, brain, blood, bones, liver, skin, etc.

Hematopoietic stem cells (HSCs) have the ability to renew themselves and to give rise to all lineages of the blood. Conditions of the aged that benefit from enhance proliferation of HSC include, for example, conditions of blood loss, such as surgery, injury, and the like, where there is a need to increase the number of circulating hematopoietic cells. Anemia is an abnormal reduction in red blood cells, which can occur from a malfunction in the production of red blood cells. Weakness and fatigue are the most common symptoms of even mild anemia. Anemia in the elderly is often due to causes other than diet, particularly gastrointestinal bleeding or blood loss during surgery. Anemia in older people is also often due to chronic diseases and folic acid and other vitamin deficiencies.

In conditions of the aged where there is a requirement for hematopoietic cell generation, a heparin binding protein composition may be administered, e.g., following incidents of blood loss, and the like.

Neural stem cells are primarily found in the hippocampus, and may give rise to neurons involved in cognitive function, memory, motor control, and the like. Neural stem and progenitor cells can participate in aspects of normal development, including migration along well-established migratory pathways to disseminated CNS regions, differentiation into multiple developmentally- and regionally-appropriate cell types in response to micro-environmental cues, and non-disruptive, non-tumorigenic interspersion with host progenitors and their progeny.

Aged individuals often suffer from a diminution of neural function. As such, the methods provided herein find use in the treatment of a variety of conditions, including traumatic injury to the spinal cord, brain, and peripheral nervous system; treatment of degenerative disorders including Alzheimer's disease, Huntington's disease, Parkinson's disease; Creutzfeldt-Jakob disease; stroke; and the like.

The methods disclosed herein may also be carried out on stem cells present in the epidermis, which give rise both to epidermal and mesenchymal tissues. Like most of the body's tissues, the skin undergoes many changes in the course of the normal aging process. The cells divide more slowly, and the inner layer of the dermis starts to thin. Fat cells beneath the dermis begin to atrophy. In addition, the ability of the skin to repair itself diminishes with age, so wounds are slower to heal. The thinning skin becomes vulnerable to injuries and damage. The underlying network of elastin and collagen fibers, which provides scaffolding for the surface skin layers, loosens and unravels. Skin then loses its elasticity. When pressed, it no longer springs back to its initial position but instead sags and forms furrows. The skin is more fragile and may bruise or tear easily and take longer to heal.

In response to damage of aged skin, for cosmetic purposes, following trauma such as burns, abrasions, etc., it may be beneficial to stimulate proliferation of stem cells. Heparin binding protein composition may be administered topically, e.g., in combination with agents to enhance penetration through the dermal layers, systemically, using implants, etc.

In many clinical situations, the bone healing condition are less ideal due to decreased activity of bone forming cells, e.g., within aged people. Within bone marrow stroma there exists a subset of non-hematopoiethic cells capable of giving rise to multiple cell lineages. These cells termed as mesenchymal stem cells (MSC) have potential to differentiate to lineages of mesenchymal tissues including bone, cartilage, fat, tendon, muscle, and marrow stroma.

A variety of bone and cartilage disorders affect aged individuals. Such tissues are normally regenerated by mesenchymal stem cells. Included in such conditions is osteoarthritis. Osteoarthritis occurs in the joints of the body as an expression of "wear-and-tear". Thus athletes or overweight individuals develop osteoarthritis in large joints (knees, shoulders, hips) due to loss or damage of cartilage. This hard, smooth cushion that covers the bony joint surfaces is composed primarily of collagen, the structural protein in the body, which forms a mesh to give support and flexibility to the joint. When cartilage is damaged and lost, the bone surfaces undergo abnormal changes. There is some inflammation, but not as much as is seen with other types of arthritis. Nevertheless, osteoarthritis is responsible for considerable pain and disability in older persons.

In conditions of the aged where repair of mesenchymal tissues is decreased, or there is a large injury to mesenchymal tissues, the stem cell proliferation may be enhanced by administration of the heparin binding protein composition.

In certain cases, the contacting may increase somatic cell proliferation by about 10% or more compared to the absence of the heparin binding protein composition. For example, the contacting may increase the somatic cell proliferation by 10%, 20%, 30%, 40%, 50%, 60%, 70%, 80%, 90%, 100%, or more compared to the absence of the heparin binding protein composition.

In some instances, the contacting may be administering the heparin-binding protein composition to the subject after the occurrence of a tissue injury, e.g., 1 or more days after the injury occurrence, such as 2 or more days after the injury occurrence. The administering of the heparin-binding protein composition may be performed 0 days to 30 days after occurrence of the injury. In certain cases, the administering may be performed 1 days to 25 days, or 3 days to 20 days, or 3 days to 15 days, or 3 days to 10 days, or 3 days to 7 days, or after 3 days to 5 days, after the occurrence of the injury.

Following delivery of heparin-binding protein composition, the subject may be given standard rehabilitative therapy and the repair of damaged and/or altered tissue may be assessed. Assessment of reparative or restorative effects may include testing for physical (e.g., muscle strength, motor skills, movement of extremities, speech, etc.) and/or cognitive function by any convenient protocol over the course of one, two, four and six weeks after administration of heparin binding protein composition.

In certain cases, the somatic cell may be a cell that has a decreased viability due to a number of conditions, such as, aging, injury, disease, and/or exposure to a toxin, such as, mutant huntingtin, hyperphosphorylated tau, prions; proteins aggregates, such as, an amyloid beta globulomer, polyglutamine protein aggregates, and the like.

In certain cases, the subject methods may be used to treat a subject having a condition characterized by neural cell death, such as, traumatic brain injury, Alzheimer's Parkinson's, Huntington's, Creutzfeldt-Jakob, and other diseases.

In certain cases, the subject methods may be used to treat a subject at risk of developing a condition characterized by neural cell death. In certain cases, a subject at risk of developing a condition characterized by neural cell death may be identified by assaying a marker(s) for the disease, such as, presence of a mutant gene, presence of other genetic markers, and the like.

The somatic cell with decreased viability may be any somatic cell as provided herein. In particular embodiments, the somatic cell may be a neuron, such as, a cortical neuron, e.g., a glutamatergic neuron.

In certain cases, a method for enhancing viability of a cortical neuron exposed to a toxin, such as, amyloid beta globulomer is provided, the method may include contacting the cortical neuron with a heparin binding protein composition.

The timing of administration of the heparin binding protein composition may be determined on a case-by-case basis and can be for therapeutic and/or prophylactic purposes.

The heparin-binding protein composition and the routes of administration may be as described in the present disclosure.

In certain cases, the contacting may increase somatic cell viability by about 2 months to about 50 years or more compared to the absence of the heparin binding protein composition. For example, the contacting may increase the somatic cell viability by 2 months, 6 months, 1 year, 3 years, 5 years, 8 years, 10 years, 15 years, 20 years, 25 years, 30 years, 35 years, 40 years, 45 years, 50 years, 55 years or more compared to the absence of the heparin binding protein composition.

The increased viability of a somatic cell may refer to prevention of loss of the cell as evidence by necrosis or apoptosis. Increase in somatic cell viability may be assayed by any method known in the art and may include assessing function of the somatic cell. For example, the method may include administering the heparin binding protein composition to a subject having or at risk of developing a neural disorder that has a specific set of symptoms. Assessing of increased neural cell viability would include monitoring the absence of development of the symptoms, where complete absence or delayed development of symptoms would indicate that the administration of the heparin binding protein composition is effective in increasing cell viability. In cases where the symptoms have appeared, the assessing would include monitoring the symptoms, where a decrease in the severity of the symptoms, a lack of or decreased rate of increase in the severity of the symptoms, or disappearance of the symptoms indicate that the administration of the heparin binding protein composition is effective in increasing cell viability.

In a specific embodiment, the heparin-binding protein composition can be used for treatment of patients by means of a short-term administration, e.g., of 1, 2, 3 or more days, up to 1 or 2 weeks, in order to obtain a rapid, significant increase in somatic cell proliferation. In another embodiment, the heparin-binding protein composition can be used for treatment of patients by means of a long-term administration, e.g., once a month, every two months, every three months, every three months, every six months every nine months, every year, every three years, or less frequently for the life time of the patient.

As effective amount of the heparin binding protein composition in the methods provided here may be determined empirically, for example, using animal models as provided herein. In vitro models are also useful for the assessment of effective amount. For example, cultures are described herein where the regenerative potential of stem cells are evaluated in the absence or presence of heparin binding protein composition.

Contacting of the somatic cell with the heparin binding protein composition may be carried out by a variety of appropriate methods. In certain embodiments, the heparin binding protein composition may be administered to a subject. The administering may be via any appropriate route, including systemic or localized routes. Routes of administration may be combined, if desired, or adjusted depending upon the pharmaceutical composition and/or the desired effect.

Also disclosed herein is a culture medium enriched for heparin binding proteins, where the culture medium is medium conditioned by growth of human embryonic stem cells. Also disclosed herein are methods for enhancing proliferation or viability of a somatic cell, where the method includes contacting the somatic cell with a culture medium enriched for heparin binding proteins, where the culture medium is medium conditioned by growth of human embryonic stem cells.

Also provided herein are methods for enhancing viability and/or proliferation of adult stem cells and/or adult progenitor cells in vitro. With explantation and in vitro culture, adult stem and progenitor cells lose stem cell function and proliferative capacity, and suffer high mortality when reintroduced in vivo. As such, the subject methods may be used to enhance proliferation and viability of explanted adult stem and progenitor cells by contacting the explanted adult stem or adult progenitor cells with heparin binding protein composition, wherein the composition includes heparin binding protein isolated from a medium conditioned by growth of human embryonic stem cells, or embryonic carcinoma cells, where the contacting is for a period of time sufficient to provide for enhanced proliferation of the explanted adult stem or adult progenitor cells compared to the absence of the heparin binding protein composition.

Routes of Administration

The heparin-protein binding composition or a cell culture medium enriched for heparin binding proteins secreted by human ES or embryonic carcinoma cells may be administered using any medically appropriate procedure, e.g., intravascular (intravenous, intraarterial, intracapillary) administration, injection into tissue, injection into cerebrospinal fluid, intracavity injection, or the like.

Where local delivery is desired, administration may involve administering the composition to a desired target tissue, such as muscle, brain, spine, etc. For local delivery, the administration may be by injection or by placement of the composition in the desired tissue or organ by surgery, for example. In certain cases, an implant, such as a cannula implant, that acts to retain the active dose at the site of implantation may be used.

In some instances, hydrogel delivery may be employed, e.g., as described in Piantino J, et al. (2006) Exp Neurol. 201:359-67; and Ma J, et al. (2007) Biomed Mater. 2:233-40. In some instances, systemic, intraperitoneal, intravascular or subcutaneous protocols are employed, e.g., as described in Pardridge W M (2008) Bioconjug Chem. 19:1327-38. In some instances, nanoparticle mediated delivery protocols may be employed, e.g., as described in Tosi G, et al. (2008). Expert Opin Drug Deliv. 5:155-74; and Ulbrich K, et al. (2008); Eur J Pharm Biopharm. 2008 Sep. 5. In some instances, intracerebral, ventricular or intrathecal delivery protocols may be employed, e.g., as described in Buchli A D and Schwab M E (2005) Ann Med. 37:556-67; and Shoichet M S, et al. (2007) Prog Brain Res. 161:385-92. In some instances, intranasal delivery protocols are employed, e.g., as described in Smith PF (2003) IDrugs. 6:1173-7; and Vyas TK, et al. (2006) Crit Rev Ther Drug Carrier Syst. 23:319-47.

Intrathecal administration may be carried out through the use of an Ommaya reservoir, in accordance with known techniques. (F. Balis et al., Am J. Pediatr. Hematol. Oncol. 11, 74, 76 (1989).

In some embodiments, the heparin-binding protein composition may be formulated to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin. Other strategies for transportation across the BBB may entail the use of endogenous transport systems, including carrier-mediated transporters such as glucose and amino acid carriers, receptor-mediated transcytosis for insulin or transferrin, and active efflux transporters such as p-glycoprotein. Alternatively, drug delivery behind the BBB is by intrathecal delivery of therapeutics directly to the cranium, as through an Ommaya reservoir.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Heparin-Binding Protein Composition

The heparin binding protein composition of the present disclosure includes heparin binding proteins secreted by pluripotent stem cells, such as, human embryonic stem cells. The compositions of the present disclosure may include heparin binding proteins isolated from a culture medium conditioned by growth of pluripotent stem cells, such as, human embryonic stem cells. In certain cases, the heparin binding protein composition may be a cell culture medium enriched for heparin binding proteins, where the culture medium is conditioned by growth of pluripotent stem cells.

Any appropriate method for isolating heparin binding proteins from a culture medium conditioned by growth of human embryonic stem cells may be used. Exemplary methods include using heparin to bind to the heparin binding proteins and isolating the bound heparin binding proteins. The heparin may be conjugated to a solid support, such as, a column, membrane, nitro-cellulose, matrix, beads, and the like. The bound heparin binding proteins may be subsequently released from the heparin by disrupting the interaction between heparin binding proteins and heparin by using an elution solution that has a high or a low pH; choatropic agent, such as, a high salt concentration; detergents; etc.

A cell culture medium enriched for heparin binding proteins, where the culture medium is conditioned by growth of pluripotent stem cells may be prepared by removing non-heparin binding proteins from the cell culture medium. For example, the conditioned medium may be processed to remove serum proteins such as albumin by using an antibody that binds to albumin, thereby enriching the medium for heparin binding proteins.

In certain cases, the heparin binding protein composition may include heparin binding proteins isolated from the conditioned growth medium and one or more proteins present in the conditioned growth medium. For example, the heparin binding protein composition may include heparin binding proteins isolated from the conditioned growth medium and a fraction of the conditioned growth medium. For example, the conditioned growth medium may be fractionated into different fractions where each fraction contains proteins in a certain size range.

"Conditioned medium" refers to a growth medium that is further supplemented with soluble factors ("culture derived growth factors") derived from pluripotent stem cells, such as iPS cells, ES cells, such as, human embryonic stem cells or embryonic carcinoma cells, cultured in the medium.

A conditioned medium may be a medium in which a pluripotent stem cell, such as iPS cells, ES cells, such as, human embryonic stem cells or embryonic carcinoma cells, has been grown for a period of 1 day-7 days.

In general, the heparin binding protein composition or a cell culture medium enriched for heparin binding proteins secreted by pluripotent stem cells are essentially free of the pluripotent stem cells. Accordingly, the heparin binding protein composition or a cell culture medium enriched for heparin binding proteins secreted by pluripotent stem cells do not have detectable numbers of pluripotent stem cells, such as, the pluripotent stem cell which secreted the heparin binding proteins.

As noted herein, the heparin binding protein composition or a cell culture medium enriched for heparin binding proteins secreted by pluripotent stem cells may include one or more heparin binding proteins that enhance somatic cell proliferation and/or viability.

In general, the conditioned media is separated from the pluripotent stem cell prior to the isolation or enriching of heparin binding proteins. The separation by methods, such as, centrifugation, filtration, precipitation, results in a conditioned medium that is essentially cell-free. In this context, "essentially cell-free" refers to a conditioned medium that contains fewer than about 10%, preferably fewer than about 5%, 1%, 0.1%, 0.01%, 0.001%, and 0.0001% than the number of cells per unit volume, as compared to the culture from which it was separated.

In certain cases, the heparin binding protein composition may not include fibroblast growth factor(s) (FGF), such as, FGF-2. In certain cases, the cell culture medium enriched for heparin binding proteins may not include fibroblast growth factor(s) (FGF), such as, FGF-2.

The medium conditioned may be conditioned from growth of any pluripotent stem cell, such as, induced pluripotent stem (iPS) cell, embryonic stem (ES) cell, embryonic carcinoma cells, human ES cell, human iPS cell, primate ES cell, primate iPS cell, mouse ES cell, mouse iPS cell, bovine ES cell, bovine iPS cell, equine ES cell, equine iPS cell, and the like.

The heparin binding protein composition may be a formulation of the heparin binding protein(s) with an appropriate carrier or diluent. In one aspect, heparin binding protein composition may be a formulation of the heparin binding protein(s) with an appropriate pharmaceutically acceptable excipient. The composition may be formulated into preparation in liquid or semi-solid or solid form, such as, solutions, injections, inhalants, gels, matrix, and the like.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available.

The subject methods are useful for both prophylactic and therapeutic purposes. The dosage of the formulation will vary widely, depending upon the nature of the condition, the frequency of administration, the manner of administration, the clearance of the heparin-binding protein from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

Formulations are typically provided in a unit dosage form, where the term "unit dosage form", refers to physically discrete units suitable as unitary dosages for human subjects, each unit containing a predetermined quantity of heparin-binding protein in an amount calculated sufficient to produce the desired effect in association with a pharmaceutically acceptable diluent, carrier or vehicle. The specifications for the unit dosage forms of the present invention depend on the particular formulation employed and the effect to be achieved, and the pharmacodynamics associated with formulation in the host.

In general, heparin-binding protein composition is administered at a dose that is effective to cause an increase in somatic cell proliferation or enhance viability of a somatic cell, but which maintains the overall health of the individual. Treatment regimens will often utilize a short-term administration of the heparin-binding protein composition; although the treatment may be repeated as necessary. The treatment regime can require administration for prolonged periods, but may be administered as a single dose monthly, semi-monthly, etc. The size of the dose administered may be determined by a physician and will depend on a number of factors, such as, the nature and gravity of the injury, disease, the age and state of health of the patient.

Methods of the present disclosure may be practiced with a variety of different types of subjects. In the methods, the subject may vary. In certain embodiments, the subjects are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits), and primates (e.g., humans, chimpanzees, and monkeys). In certain embodiments, the subjects are humans.

Kits

The present disclosure also provides a pharmaceutical pack or kit comprising one or more containers filled with one or more of the heparin binding protein compositions described herein. Kits may contain unit doses of the heparin binding protein compositions. Associated with such container(s) can be a notice in the form prescribed by a governmental agency regulating the manufacture, use or sale of pharmaceuticals or biological products, which notice reflects approval by the agency of manufacture, use or sale for human administration.

Screening Methods

Methods for identifying modulators of somatic cell proliferation and/or viability are provided. Any somatic cell described herein may be used in the screening methods.

In certain embodiments, a method for identifying modulators of somatic cell proliferation may include contacting a somatic cell with heparin binding protein composition, wherein the composition comprises heparin binding protein isolated from a medium conditioned by growth of human embryonic stem cells, in the presence of a candidate agent wherein an increase or decrease in the somatic cell proliferation compared to the absence of the candidate agent identifies the candidate agent as a modulator of somatic cell proliferation.

In certain embodiments, the method may be for identifying candidate agents that increase somatic cell proliferation. In such methods, an increase in the somatic cell proliferation compared to the absence of the candidate agent identifies the candidate agent as an enhancer of somatic cell proliferation.

Also provided are screening methods to identify candidate agents that increase viability of a somatic cell. The screening method may include contacting the somatic cell with heparin binding protein composition, wherein the composition comprises heparin binding protein isolated from a medium conditioned by growth of human embryonic stem cells, in the presence of the candidate agent, wherein increased viability of the somatic cell as compared to the absence of the candidate agent identifies the candidate agent as an enhancer of somatic cell viability.

Candidate agents of interest for screening include biologically active agents of numerous chemical classes, primarily organic molecules, although including in some instances, inorganic molecules, organometallic molecules, immunoglobulins, genetic sequences, etc. Also of interest are small organic molecules, which comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Compounds may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A plurality of assays may be run in parallel with different concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in somatic cell proliferation/viability.

The screening methods may be carried out using any somatic cell of interest. The somatic cells may be as provided in the present disclosure.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Materials and Methods

Animals

Young (2-3 month old) and old (22-24 month old) C57BL6/J mice were purchased from the Jackson Laboratory and the NIH. The animal experimental procedures were performed in accordance with the Guide for Care and Use of Laboratory Animals of the National Institutes of Health, and approved by the Office of Laboratory Animal Care, UC Berkeley.

Antibodies

Antibodies for phospho-ERK1/2, ERK1/2, and cleaved caspase 3 were purchased from Cell Signaling. Laminin and Actin antibodies were from Sigma. FGF2 antibody was from Santa Cruz, Pax7 and eMyHC antibodies were from Hybridoma Bank, BrdU was from Abcam, and Map2 antibody was from BD Biosciences.

Muscle fibers and Muscle Stem cell Isolation

Uninjured TA muscle was dissected from healthy young and old mice and incubated at 37C in digestion medium (250 U/mL Collagenase type II in DMEM medium, buffered with 30 mM HEPES) for 1 hour (Bischoff, R., Developmental biology, 1986. 115(1): p. 129-139). Digested muscle was gently triturated and myofibers were collected. Myofibers were further digested with 1 U/mL Dispase and 40 U/mL Collagenase type II to liberate muscle stem cells (Conboy, M. J. and I. M. Conboy. Methods Mol Biol, 2010. 621: p. 149-63). Muscle stem cells were cultured in DMEM with serum from the same age mouse.

Immunofluorescence Analysis

Cells were fixed with 4% PFA for 10 minutes before permeablization with 0.1% Triton-X 100 for 30 minutes. Then cells were then immunostained for Pax? (Hybridoma Bank) and ki67 (Abcam). Primary antibodies used for staining cortical human neurons were: mouse anti-MAP2 (1:500, BD Biosciences), rabbit anti-cleaved caspase 3 (1:100, Cell Signaling). For muscle section immunostaining, an uninjured TA muscle was sectioned at 10 um and stained for FGF2 (Santa Cruz) and laminin (Sigma).

Western blotting

Muscle stem cells or myofibers were lysed in RIPA buffer containing 1× protease inhibitor (Roche). The protein concentration was determined by Bradford assay (Bio-Rad). Cell or fiber lysates were resuspended in 1× Laemmli buffer (Rio-rad), boiled for 5 minutes and separated on precast TGX gels from Biorad. The proteins were then transferred to PVDF membrane (Millipore) and blotted with the desired antibodies.

Cell Culture

Rat NPCs were cultured in DMF12 (Gibco) with 5% N2 and 10 ng/mL FGF2, on laminin and polyornithine coated plates. For experimental conditions, cells were plated at 40,000 cells/well in coated 8-well chamber slides and cultured for 12-16 hours at 37 C in 10% CO2 incubator prior to fixation with 70% ethanol at 4 C. Adult human myoblasts were cultured and expanded in human growth medium (Ham's F-10 (Gibco), 10% Bovine Growth Serum (Hyclone), 30 ng/mL FGF2, and 1% penicillin-streptomycin on Matrigel (BD Biosciences) coated plates (1:100 matrigel: PBS), at 37 C and 5% $CO_2$. For experimental conditions, cells were plated at 10,000 cells/well in Matrigel coated 8-well chamber slides (1:100 Matrigel: PBS), and cultured for 72 hours with daily re-feedings at 37 C in 10% CO2 incubator prior to fixation with 70% ethanol at 4 C. Mouse myoblasts were cultured and expanded in mouse growth medium: Ham's F-10 (Gibco), 20% Bovine Growth Serum (Hyclone), 5 ng/mL FGF2 and 1% penicillin-streptomycin on Matrigel coated plates (1:300 matrigel: PBS), at 37 C and 5% CO2. For experimental conditions, cells were plated at 40,000 cells/well on Matrigel coated 8-well chamber slides (1:100 matrigel: PBS) and cultured for 24 hours at 37 C in 10% $CO_2$ incubator prior to fixation with 70% ethanol at 4 C.

Human embryonic stem cells (H9 and H7 lines), were cultured on diluted Matrigel (1:30), in mTeSR-1 (Stem Cell Technologies), according to manufacturer's recommendations. hESCs were differentiated after plating in mTeSR-1 by changing the medium to DMEM/F12 with 10% Bovine Growth Serum (Hyclone), and culturing for an additional 6-8 days. Cells were washed with Opti-MEM (Gibco) and then cultured in Opti-MEM for 18 hours prior to collection as hESC-Conditioned Opti-MEM (hESC-Conditioned Medium) and stored at −80 C.

All experiments using a MEK inhibitor were treated with 10 micromolar MEK1/2 Inhibitor (U0126, Cell Signaling Technologies).

Cell Culture and Cortical Differentiation of Human Pluripotent Stem Cells

The H1 (WiCell) and hESC line was cultured on Matrigel-coated cell culture plates (BD) in mTeSR-1 maintenance medium (Stem Cell Technologies). In adherent conditions, hPSCs were seeded at a density of 5×104 cells/cm2 in growth medium. At 50% confluence, the medium was gradually changed to neural basal medium (Invitrogen) containing N2 and B27 (Invitrogen). SMAD signaling inhibitors LDN193189 (Stemgent, 1 μM) and SB432542 (Tocris Biosciences, 10 μM) were added from day 1 to day 7 of neural induction. Cyclopamine (Calbiochem, 400 ng/ml) and FGF-2 (Peprotech, 10 ng/ml) were added from days 3-14 of differentiation. After 12-14 days, cells were mechanically passaged into poly-L-ornithine (Sigma Aldrich) and laminin (Invitrogen, 20 μg/ml) coated plates and allowed to undergo maturation for 3-6 weeks. BDNF (10 ng/ml, Peprotech) was added to cultures one week after initiation of neuronal maturation. For EB mediated neural differentiation, PSCs were aggregated for 4 days in ultra low-attachment plates (Corning) and then seeded on Matrigel-coated plates. Cyclopamine (5 μM) and FGF-2 (10 ng/ml) were added to the cultures the following day until day 12 of neural induction. At day 14, structures with a rosette-like morphology were mechanically isolated and plated on poly-L-ornithine and laminin coated plates and allowed to undergo neuronal maturation for 4 weeks. BDNF (10 ng/ml) was added to the cultures one week after rosette isolation.

Globulomer Preparation

The Aβ42 globulomer was prepared as described (Barghorn et al., 2005, J Neurochem. 95, 834-47; Yu et al., 2009, Biochemistry. 48, 1870-7). Alkaline pretreatment of Aβ42 and preparation of low molecular weight Aβ by filtration protocols were used before beginning the globulomer preparation as previously described (Yu et al., 2009, supra). After the 18-20 h incubation, the globulomer sample were concentrated to ~500 mM via centrifugation and dialyzed into PBS before centrifuging the sample at 10,000 g for 10 min to remove aggregates in the pellet. The supernatant was saved, and the absorbance was measured at 276 nm wavelength to measure the concentration (extinction coefficient=1390 M−1 cm−1).

Immunocytochemistry

For immunoflourescence assays, human and mouse myoblasts were given a 4 hour and 2 hour 300 μm BrdU pulse, respectively. Cells were then permeabilized in PBS +0.25% Triton X-100 and incubated with primary antibodies overnight at 4° C. in PBS +2% FBS. Antigen retrieval was performed via a 10 minute 4 N HCl treatment followed by PBS wash. Primary staining was performed overnight with species-specific monoclonal antibodies for mouse anti-embryonic Myosin Heavy Chain (eMyHC) (eMHC hybridoma (clone 1.652), Developmental Studies Hybridoma Bank) and Rat-BrdU (Abcam Inc. ab6326) for myoblasts, and Goat-Sox2 (Santa Cruz) for rNPCs. Secondary staining with fluorophore-conjugated, species-specific antibodies (Donkey anti-Rat-488, #712-485-150; Donkey anti-Mouse-488, #715-485-150; Donkey anti-Rat-Cye3 #712-165-150; or donkey anti-Mouse-Cye3 #715-165-150; all secondary antibodies from Jackson ImmunoResearch) was performed for 1 hour at room temperature at a 1:500 dilution in PBS +2% FBS. Nuclei were visualized by Hoechst staining, and samples were analyzed at room temperature with a Zeiss Axio Imager Al, and imaged with an Axiocam MRC camera and AxioVision software. Human and mouse myoblasts were imaged at 10× and 20× magnification, respectively.

For cell quantification, 25-50 20× images per replicate were taken on the Molecular Devices ImageXpress Micro automated epifluorescence imager, followed by automated cell quantification using the multiwavelength cell scoring module within the MetaXpress analysis software.

Heparin Bead Depletion of hESC-Secreted Proteins from hESC-Conditioned Medium

Heparin-Agarose Type I Beads (H 6508, Sigma Aldrich) were washed with molecular grade water and preconditioned in 1 mL OptiMEM as recommended by manufacturer. hESC-conditioned medium was incubated with Heparin-Agarose Beads for 2 hours shaking at 4° C. Beads and all medium were separated by centrifugation. Myoblasts were treated with depleted medium after two rounds of centrifugation and separation of beads and medium so as to remove all residual beads from depleted hESC-conditioned medium.

Heparin Bead Bound Proteins Elution and Purification

After depleting hESC-Conditioned OptiMEM, the protein bound heparin beads were washed two times for 10 minutes at 4° C. in 1 ml PBS +0.05% Tween. Proteins were eluted twice for 15 minutes at 4° C. in 400 µl of elution buffer (0.01M Tris-HCl pH 7.5+1.5M NaCl+0.1% BSA) to collect proteins in a total of 800 µl of elution buffer. The proteins were purified by diffusion dialysis by a 2 hour dialysis shaking at 4° C. in 500 ml McCoy's 5A Medium (Gibco) followed by overnight dialysis shaking at 4° C. in 200 ml OptiMEM (Gibco). The eluted heparin beads were re-suspended in 800 µl OptiMEM and stored overnight at 4° C. One hour after plating, mouse myoblasts were treated with respective mediums for 24 hours prior to 2 hour BrdU pulse and fixation in 70% ethanol.

Muscle Injury

Isoflurane was used to anesthetize the animal during the muscle injury procedure.

For bulk myofiber satellite cell activation, gastrocnemius muscles were injected with cardiotoxin 1 (Sigma) dissolved at 100 micrograms per milliliter in PBS, at 4 sites of 10 microliters each for each muscle. Muscles were harvested 3 days later. For focal injury, to assay regeneration in vivo, 5 microliters of 0.5 milligram per milliliter CTX was injected at two sites to the middle of the tibialis anterior, and muscle harvested 5 days later.

Tissue Immunofluorescence and Histological Analysis

Muscle tissue was dissected, flash frozen in OCT compound (Tissue Tek; Sakura) and cryo-sectioned at 10 micrometers, as previously described (Conboy et al., 2003). Cryo-sectioning was performed through the entire volume of muscle (typically 50-70 sections total, done at 200 µm intervals), thereby serially reconstituting the entire tissue, ex vivo. Muscle sections were stained with aqueous hematoxylin and eosin (H&E), as per the manufacturer's instructions (Sigma-Aldrich). Regeneration and myogenic potential was quantified by examining injury sites from representative sections along the muscle (spanning the volume of injury), then by measuring the injured/regenerating area using Adobe Photoshop Elements. Myofiber regeneration was quantified by counting total newly regenerated fibers and dividing by the regeneration area. Immunostaining was performed as described (Conboy, M. J., et al., Methods Mol Biol, 2010. 621: p. 165-73). Briefly, after permeabilization in PBS +1% FBS +0.25% Triton-X-100, tissues and cells were incubated with primary antibodies in staining buffer (PBS+1% FBS) for 1 h at room temperature, followed by 1 h incubation fluorochrome-labeled secondary antibodies (ALEXA at 1:1000). BrdU-specific immunostaining required an extra step of 2 M HCl treatment before permeablization.

Example 1 mTeSR-1 Growth Medium has Pro-myogenic Activity, which is Due to the High Levels of FGF-2, and hESC-secreted Factors Act Independently of Recombinant FGF-2

Figure 1:
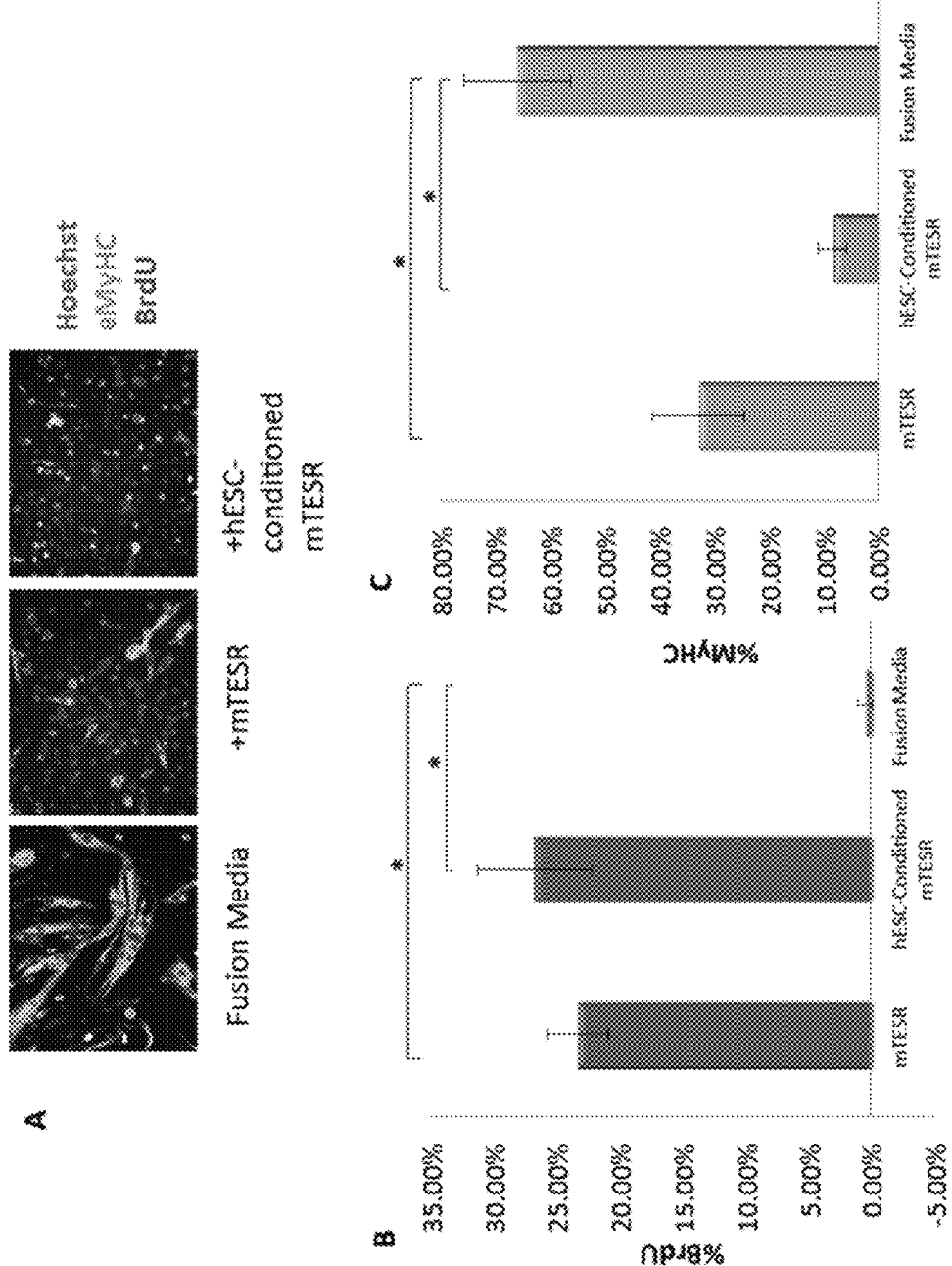
FIG. 1. Both mTeSR-1 and hESC-Conditioned mTeSR-1 increase primary myoblast and satellite cell Proliferation and inhibit Differentiation. (A) Primary Mouse Myoblasts were cultured for 24 hours in 50% fusion/differentiation medium (DMEM, 2% horse serum) plus 50% of the specified medium. A 2 hour BrdU pulse was performed before cell fixation to label proliferating cells. Immunofluorescence was performed for eMyHC (green) and BrdU (red), with Hoechst (blue) labeling all nuclei. Representative images are shown. Proliferation and differentiation of fusion-competent myoblasts were quantified by cell scoring in 25 random fields of each condition using a Molecular Devices automated imager and MetaXpress cell scoring software. Results are displayed as the mean percent of BrdU+ (B) or eMyHC+ (C) proliferating or differentiating cells +/−SD, respectively. N=4*P<4×10$^{-10}$ for BrdU+ myoblasts incubated in 50% mTeSR-1 as compared to myoblasts incubated in just fusion medium, or 50% hESC-conditioned mTeSR-1 as compared to myoblasts incubated in just fusion medium. *P<0.005 for eMyHC+ fusing myoblasts in 50% mTeSR-1 as compared to myoblasts incubated in fusion medium alone, and *P<9× 10$^{-5}$ for eMyHC+ fusing myoblasts in 50% hESC-conditioned mTeSR-1 as compared to myoblasts incubated in just fusion medium. (D) Old injury activated myofiber-associated satellite cells were isolated at 3 days post cardiotoxin-induced muscle injury, and cultured overnight in 50% DMEM/F12 with 10% old serum, and 50% of the medium specified, followed by a 2 hour BrdU pulse to label proliferating cells before cell fixation. Immunofluorescence was performed with Desmin (green) and BrdU (red), with Hoechst (blue) labeling all cell nuclei. Representative images are shown and demonstrate that both hESC-conditioned mTeSR-1 and mTeSR-1 have a pro-myogenic effect on activated satellite cells. (E) Proliferating Desmin+/BrdU+ satellite cells were quantified by cell scoring in multiple random fields of each condition. Results are displayed as the mean percent of BrdU+/Desmin+ proliferating satellite cell cells +/−SD. N=3, *P<0.05 for satellite cells in 50% mTeSR-1 as compared to satellite cells incubated in just basal medium with old serum, and *P<0.001 for satellite cells in 50% hESC-conditioned mTeSR-1 as compared to satellite cells incubated in just basal medium with old serum. (F) Undifferentiated hESCs that were grown in mTeSR-1 medium were washed 0-3 times with Opti-MEM, followed by overnight incubation in Opti-MEM and collection of the resulting conditioned Opti-MEM. The hESC-conditioned Opti-MEM was spun down to remove cell debris, before addition to myoblasts as a 50/50 mix with myogenic fusion medium for culture overnight. A 2 hour BrdU pulse was performed to label proliferating cells prior to cell fixation and immunofluorescence was performed with eMyHC and BrdU, with Hoechst labeling all cell nuclei (images not shown). Proliferating and differentiating cells were quantified by cell scoring 25 random fields of each condition using an automated imager and MetaXpress cell scoring software. Results are displayed as the mean percent of BrdU+ or eMyHC+ proliferating or differentiating cells +/−SD, respectively. N=2
Figure 1:
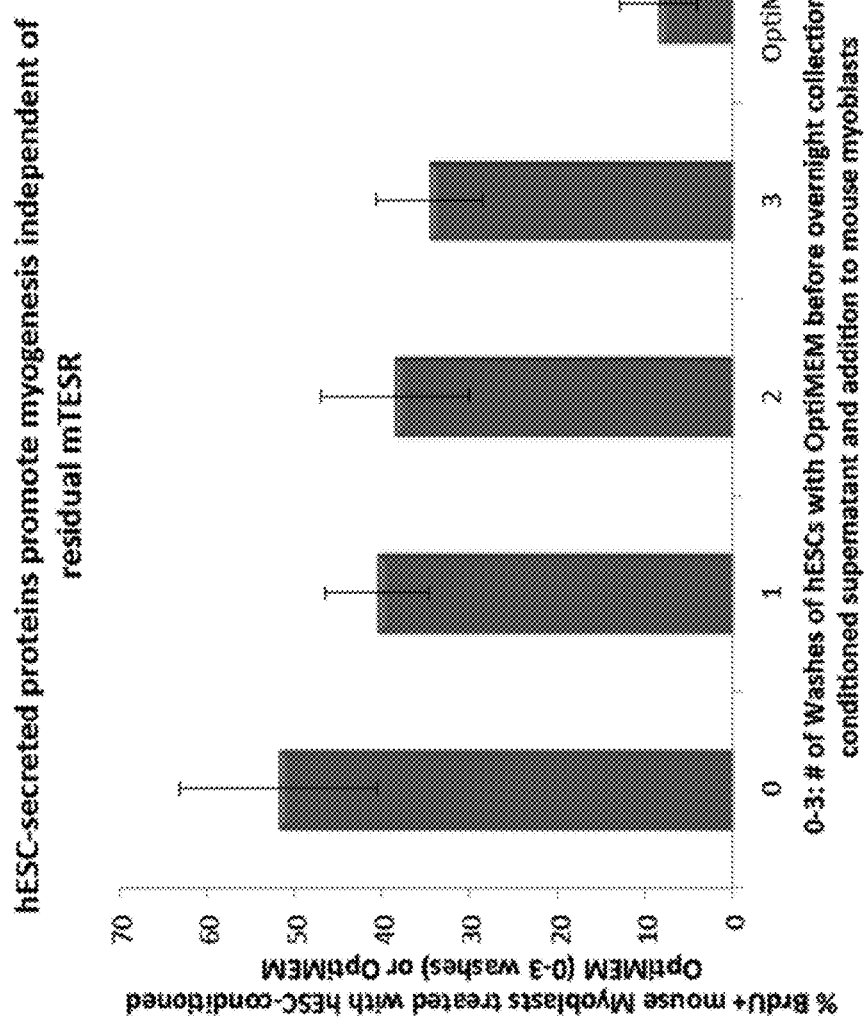

Our previous work established that injection of hESCs—which were cultured on mouse embryonic fibroblasts (MEF) and in standard, highly mitogenic, embryonic cell growth medium—enhanced old muscle regeneration (Carlson, M. E. and I. M. Conboy, Aging Cell, 2007. 6(3): p. 371-82). In our more recent work, the hESCs have been cultured in mTeSR-1 (Stem Cell Technologies), a defined feeder-free medium which is also highly mitogenic (Ludwig, T. E., et al., Nat Methods, 2006. 3(8): p. 637-646), and we investigated whether and to what degree the pro-myogenic effects of hESC-conditioned medium was due to the residual activity of the hESC growth/expansion medium. Primary muscle progenitor cells (myoblasts) were cultured overnight in a mitogen-low fusion medium that typically induces differentiation of myoblasts into multinucleated eMyHC+ myotubes. The enhancement of myogenic cell proliferation and inhibition of differentiation was assayed by BrdU uptake for the last 2 hours of culture, after which cells were fixed and used for immunofluorescence with anti-BrdU and anti-MyHC specific antibodies. When primary myoblasts were cultured in 50% fusion medium plus 50% hESC-conditioned mTeSR-1 or 50% unconditioned mTeSR-1, both media compositions induced proliferation and inhibited differentiation of these myogenic cells, though medium containing hESC-conditioned mTeSR-1 inhibited differentiation more significantly (FIG. 1A, quantified in 1B and 1C). To confirm these data with muscle stem cells, injury-activated satellite cells associated with myofibers were isolated from old muscle and cultured overnight in a 50/50 mix of Opti-MEM containing 5% old mouse serum and hESC-conditioned mTeSR-1 or mTeSR-1. Both conditioned and not-conditioned mTeSR-1 media enhanced the regenerative capacity of satellite cells that were isolated from injured old muscle, based on the numbers of de-novo generated BrdU+/Desmin+ muscle progenitor cells (FIG. 1D, quantified in 1E). These results demonstrate that embryonic stem cell culture medium itself has pro-myogenic effects. To investigate whether hESC-conditioned Opti-MEM exhibits pro-regenerative effects due to the hESC-secreted proteins, and not because of residual mTeSR-1, we washed the hESC culture wells multiple times with Opti-MEM prior to incubation for conditioning the Opti-MEM, and found that even after 3 washes, hESC conditioned the Opti-MEM to yield the same potent pro-regenerative effect on myoblasts (FIG. 1F). These results demonstrate that while mTeSR-1 supplementation promotes myoblast proliferation, other factor(s) produced by hESCs independently enhance the regenerative capacity of muscle stem and progenitor cells.

Figure 2:
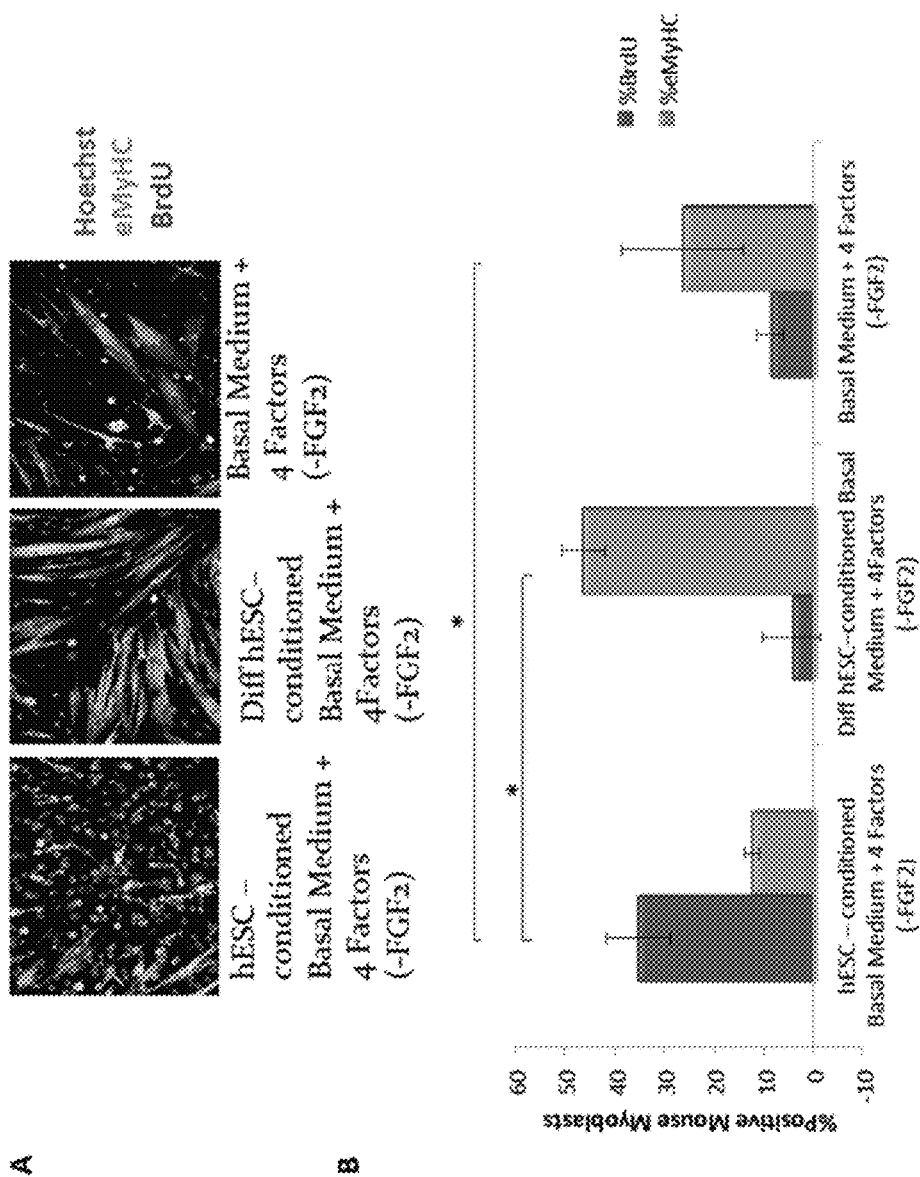
FIG. 2. hESC-conditioned medium enhances myogenic proliferation in the absence of FGF2 in mTeSR-1 growth medium. (A) Primary myoblasts were cultured for 16 hours in 50% fusion/differentiation Medium+50% of the specified medium. A 2 hour BrdU pulse was performed before cell fixation to label proliferating cells. Immunofluorescence was performed for eMyHC (green) and BrdU (red), with Hoechst (blue) labeling all nuclei. Representative images demonstrate that hESC-conditioned medium lacking FGF2 increases myoblast proliferation and inhibits differentiation. (B) Proliferation and differentiation of fusion-competent myoblasts were quantified by cell scoring in 50 random fields of each condition using an automated imager and MetaXpress cell scoring software. Results are displayed as the mean percent of BrdU+ or eMyHC+ proliferating or differentiating cells +/−SD, respectively. N=4, *P<2×10$^{-12}$ for hESC-conditioned basal medium with 4 mTeSR-1 ingredient components (lacking FGF2) as compared to differentiation hESC-conditioned basal medium with 4 mTeSR-1 ingredient components (also lacking FGF2), and for hESC-conditioned basal medium with 4 mTeSR-1 ingredient components (lacking FGF2) as compared to myoblasts incubated in basal medium with 4 mTeSR-1 ingredient components (lacking FGF2).

To understand the pro-myogenic effects of mTeSR-1 in greater detail, we addressed the role of FGF-2, which is present at high concentration in mTeSR-1 (over 50 nanograms per milliliter, ~10 times higher than the doses used in conventional culture of muscle progenitor cells). Our hypothesis was that the FGF-2 in mTeSR-1 enhances myoblast and satellite cell proliferation, partially masking the effects of the hESC-produced factors in hESC-conditioned mTeSR-1. To test this hypothesis, we incubated hESCs in a basal medium that had the other growth and signaling factors present in mTeSR-1 (TGF-beta, GABA, pipecolic acid and Lithium Chloride, (Ludwig, et al, supra)), but lacked FGF2, and compared the pro-myogenic effects of this FGF-free hESC-conditioned mTeSR-1 analog with the effects of the same mTeSR-1 analog that was not conditioned by the hESCs. Without FGF-2, the mTeSR-1 analog lacked pro-regenerative effects on myoblasts (FIG. 2A, quantified in 2B). On the other hand the very same mTeSR-1 analog lacking FGF-2, but conditioned by hESCs, significantly enhanced myoblast proliferation and inhibited differentiation, while conditioning of this mTeSR-1 analog lacking FGF-2 by differentiated hESC derived cells resulted in the absence of pro-myogenic properties (FIG. 2A, quantified in 2B). These data demonstrate that the pro-myogenic effects of mTeSR-1 are due to the high concentration of FGF-2, and that it is not simply residual FGF-2 from mTeSR-1 that is responsible for the enhancement of myogenesis by the hESC-conditioned medium.

Example 2

FGF-2 Signaling and Satellite Cell Proliferation are not Increased with Age

Figure 3:
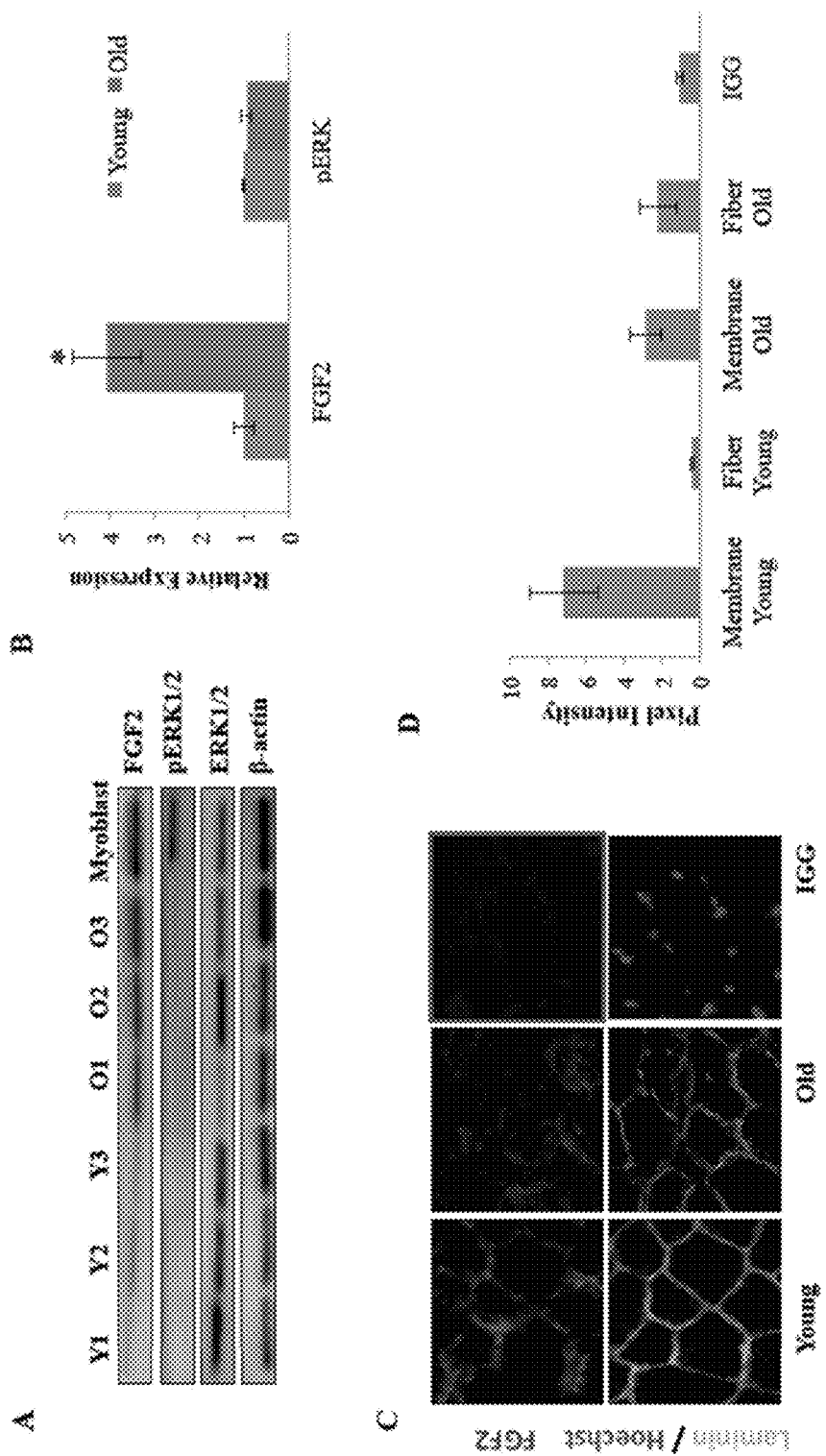
FIG. 3. Age-dependent comparison of FGF2 and pERK levels and localization in muscle fibers. (A) Protein was isolated from freshly-derived uninjured myofibers of young and old mice and the levels of FGF2 and phospho-ERK1/2; total ERK1/2 and cytoplasmic beta-actin were analyzed by Western blotting, using specific antibodies. Representative data are shown. (B) Relative protein expression was quantified in 3 young and 3 old mice by normalization of FGF-2 to beta-actin and normalization of pERK to total ERK; significantly higher levels of FGF-2, but not of pERK were detected in the old myofibers, as compared to young (n=3, * P<0.05). (C) Tibialis anterior (TA) muscle from 2 young and 2 old mice were sectioned and immunostained for laminin (green) and FGF2 (red). Hoechst (blue) labels all nuclei. Representative images demonstrate the presence of FGF-2 and laminin in muscle compartments, as compared to the negative IgG control and higher FGF-2 levels seem to be present in the laminin+ basement membranes of the young myofibers, as compared to old. (D). The pixel density of FGF-2 that co-localizes with laminin+ basement membrane vs. the internal regions of the myofibers was determined in 30-40 areas of each cryosection of 3 muscle tissue slides from young and old muscle, using Image J software. Preferential localization of FGF-2 in the basement membrane was identified in young muscle, while in the old tissue, FGF-2 was mis-localized to the center of the myofibers and away from the basement membrane, n=3, *P<0.05.

FGF-2, which often functions as a mitogen, was recently reported to contribute to the aging and depletion of mouse satellite cells. However, the canonical model of muscle stem cell aging postulates that a decline in such mitogens over time leads to reduced activation of satellite cells that are resident to old tissue (Conboy, I. M. and T. A. Rando, Cell Cycle, 2012. 11(12): p. 2260-7; Grounds, M.D., Ann. N.Y. Acad. Sci., 1998. 854: p. 78-91; onboy, I. M. and T. A. Rando, Cell Cycle, 2005. 4(3): p. 407-410), so we explored these phenomena in more detail. The levels of FGF-2 were determined by Western Blotting in muscle fibers that were derived from Tibialis Anterior (TA) and Gastrocnemius (Gastroc) muscle of young and old mice. As shown in FIG. 3A (quantified in 3B), a significant increase in FGF-2 protein was observed with age in myofibers, consistent with Chakkalakal et al. FGF-2 signals through the MAPK/pERK pathway, so we analyzed the levels of pERK in myofibers derived from young and old uninjured muscle. Interestingly, as shown in FIG. 3A (quantified in 3B), no age-specific increase in pERK was found, and the levels of this key effector were very low in cells from both ages, despite the high levels of FGF-2 in protein lysates derived from old muscle fibers. Also, a myoblast control indicates that pERK detection was sensitive (FIG. 3A). To understand these data, we examined the presence and localization of FGF-2 in the intact young and old muscle, using 10 micron cryosections. FGF-2 and laminin were detected with specific antibodies and resolved by immunofluorescence. As shown in FIG. 3 C (quantified in 3D), FGF-2 was localized in the basement membrane of young muscle, while in the old muscle, FGF-2 was present less in the basement membrane and more in the cytoplasm of the myofibers (e.g. away from its receptors in muscle stem cells). These data suggest that the relatively higher levels of FGF-2 in old muscle do not necessarily represent ligand that is available for signaling in satellite cells. Additionally, these results indicate that detection of elevated FGF-2 in the old muscle might be due to its over-expression within the old muscle fiber itself, or alternatively, due to "washing" of extracellular FGF-2 from young muscle during tissue dissociation when the basement membrane is digested with collagenase and dispase, and tissue integrity is perturbed (Bischoff, R., Developmental biology, 1986. 115(1): p. 129-139).

Figure 4:
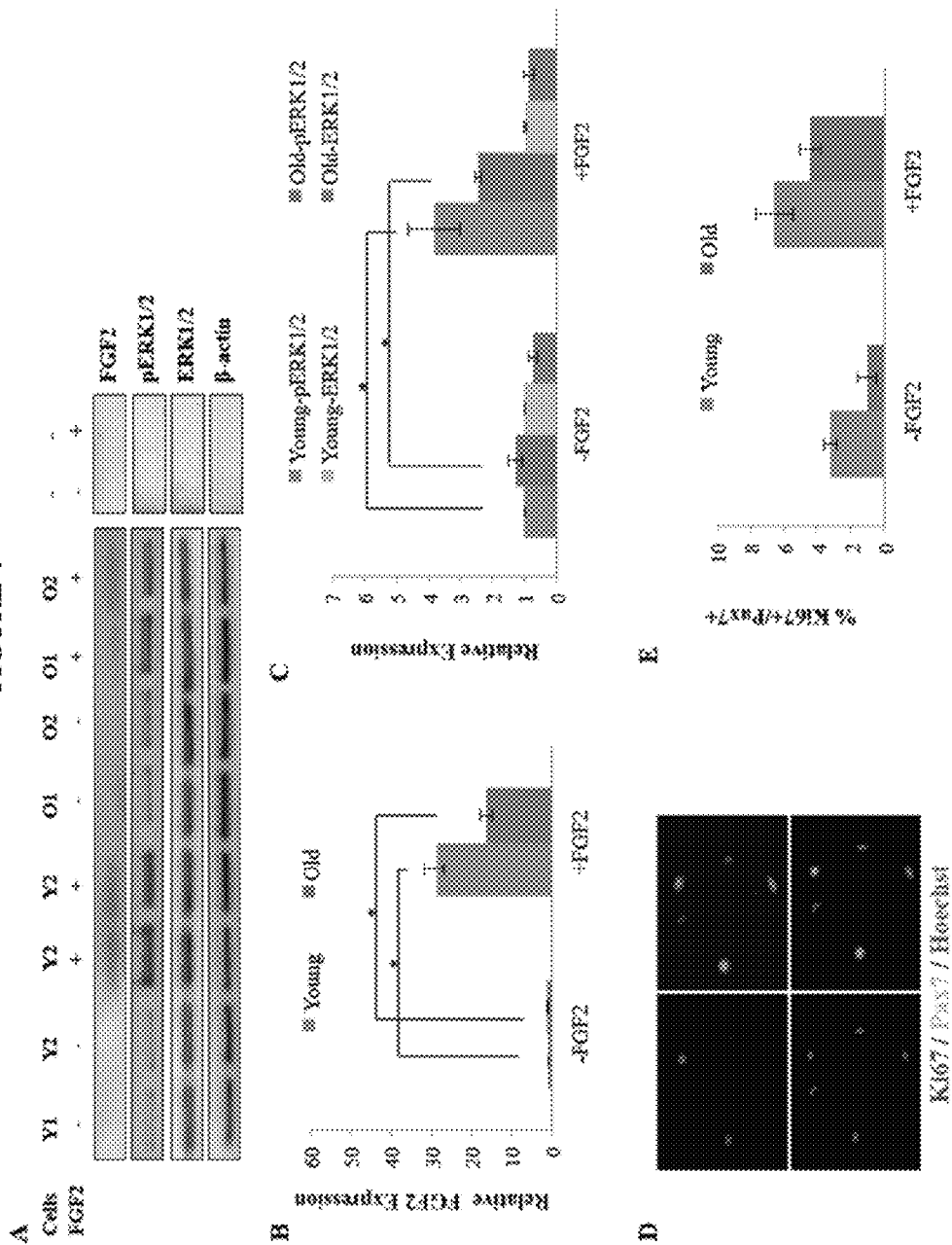
FIG. 4. Age-related comparison of FGF2 and pERK levels in muscle stem cells derived from uninjured tissue and of proliferation of these cells. (A) Quiescent muscle stem cells were isolated from uninjured young and old muscle as described in Methods. The cells were treated (or not) with FGF2 (10 ng/ml) for 30 minutes before being lysed and analyzed for the levels of FGF2, phospho-ERK1/2, total ERK1/2 and beta actin by Western Blotting. Representative images are shown. (B) Relative protein expression of FGF- 2, pERK and total ERK were quantified from 3 young and 3 old mice, using beta-actin for normalization. The levels of FGF-2 were equally undetectable in young and old satellite cells, however, added FGF-2 was clearly detected in the cells of both ages after ~2min exposure (but was not detected in accelular samples even after 10 min exposure); the levels of pERK and total were equally low in young and old satellite cells and pERK, but not total ERK, was, as expected, induced by added FGF-2. n=3, *P<0.05. (C-E) Muscle stem cells from resting muscle were treated (or not) with FGF2 (10 ng/ml) for 24 hours before immunostaining for Ki67 and Pax7. Percent of Ki67+/Pax7+ proliferating myogenic cells were quantified. No age-specific increase in cell proliferation was detected in satellite cells isolated from old uninjured muscle, and in contrast, more proliferating satellite cells were observed in the cultures derived from young muscle. Added FGF-2 enhanced the proliferation of both young and old muscle stem cells in these overnight cultures. n=3, *P<0.05.
Figure 5:
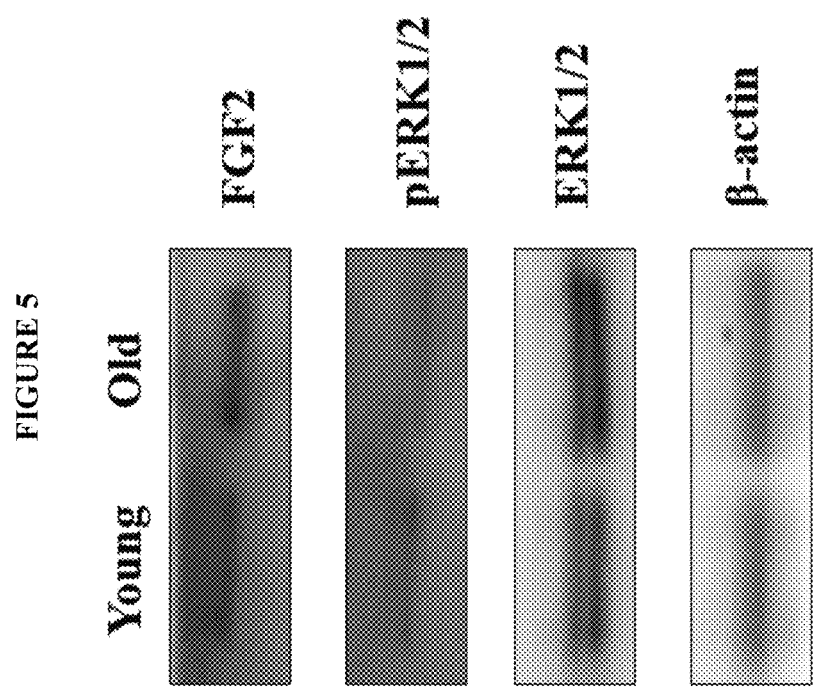
FIG. 5. Expression of FGF2 in quiescent muscle stem cells from young and old mice. Muscle stem cells were isolated from young and old uninjured muscle, as described in Methods. The cells were immediately lysed for Western blotting without culturing and the expression of FGF2, phosphor-ERK1/2, ERK1/2 and β-actin were analyzed. 30 minutes of enhanced chemiluminescence exposure was used for detection of FGF-2, while pERK, total ERK and actin were detected after 2 min, 30 sec and 30 sec exposure, respectively. Low and age-independent levels of FGF-2 and pERK were detected in satellite cells that were derived from uninjured young and old TA muscle.

To confirm and extend upon these findings, we isolated muscle stem cells from uninjured young and old TA and Gastroc muscle and treated them with FGF-2 for 30 minutes, after which the levels of FGF-2, pERK, and total ERK were determined in these freshly isolated stem cells. As shown in FIG. 4 A, B, endogenous FGF-2 was undetectable in either young or old muscle stem cells upon isolation, but the added FGF-2 was clearly present in these satellite cells after 30 minutes. Young and old satellite cells were harvested after just 30 minutes of culture, thus, the FGF-2 protein detected in cultures, which were treated with recombinant FGF-2 is unlikely to represent de-novo expression. Satellite cells were lifted from the plates with PBS and washed prior to their lysing for Western Blotting, and it was thus unlikely that any residual, non-cell associated recombinant FGF-2 from media or plates would contaminate cell lysates. To test this directly and definitively, we performed a control with a matrix-coated but cell-free plate that was identically treated with FGF-2, and found no detectable recombinant FGF-2 in the solution (FIG. 4A). Hence, the FGF-2 detected in protein lysates of young and old satellite cells incubated with this growth factor likely reflects ligand that is bound to its specific receptors. In support of this conclusion, recombinant FGF-2 induced pERK in both young and old satellite cells (FIGS. 4 A and C). In agreement with non-detectable endogenous FGF-2 in both young and old satellite cells, very low levels of pERK that did not differ with age were observed in these muscle stem cells resident to tissue that was neither injured nor treated with recombinant FGF-2 (FIGS. 4 A and C). To determine whether low levels (as opposed to none) of FGF-2 can be detected in the muscle stem cells, another independent experiment was performed with a prolonged enhanced chemiluminescence exposure of the Western Blots. As shown in FIG. 5, low levels of FGF-2 could be indeed detected in muscle stem cells after a 30 minute exposure, but once again, there was no age-specific difference in either FGF-2 or in pERK. These results suggest that FGF-2 does not signal in either young or old satellite cells that reside in non-injured skeletal muscle.

Figure 6:
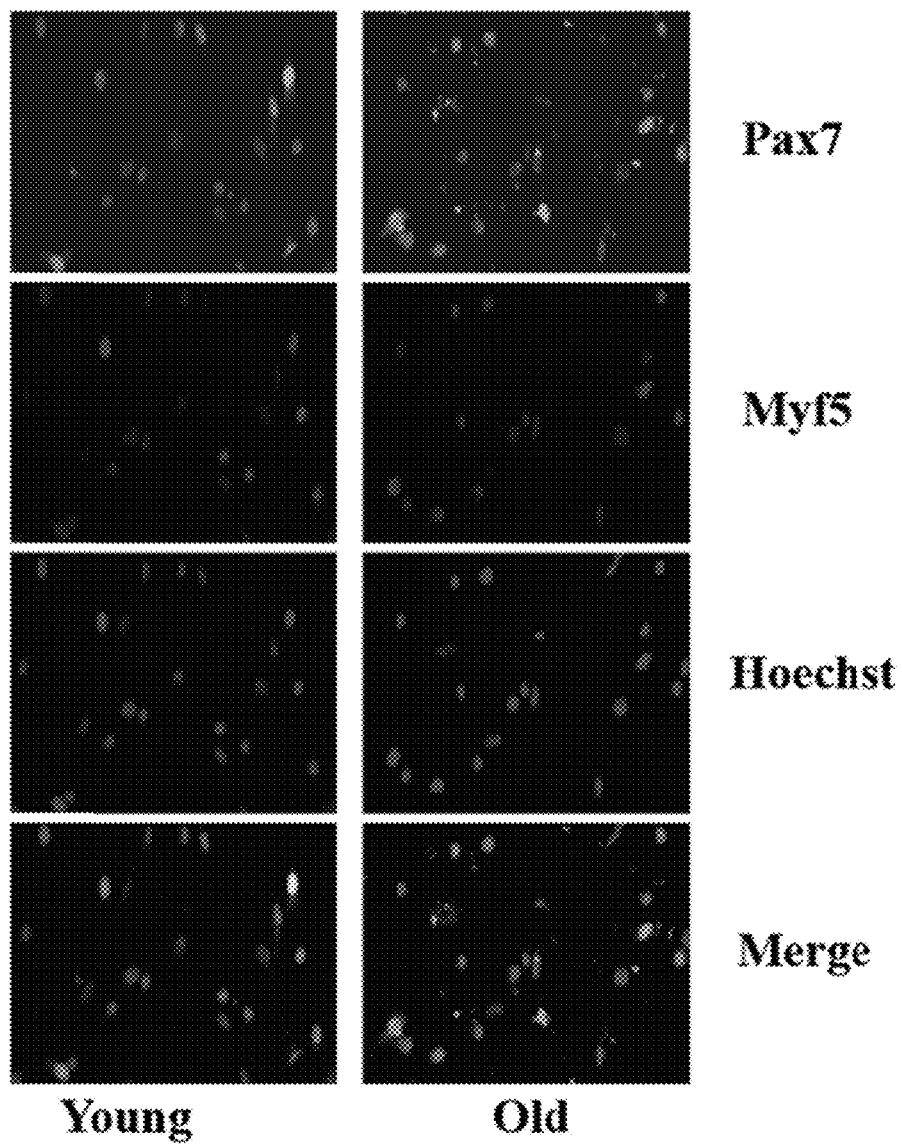
FIG. 6. Myogenic marker expression in young and old muscle stem cells.

To directly examine cell proliferation, satellite cells were isolated from non-injured young and old tissue and were cultured with or without FGF-2 overnight, after which the levels of the proliferation marker Ki67 were determined in Pax7+ satellite cells. Muscle stem cells for this and other experiments were isolated with high and equal purity from young and old mice, as shown in FIG. 6. Neither young nor old cells were lost during overnight culturing, as the numbers were similar to initial plating, and no age-specific loss was observed, based on the cell counts. As shown in FIGS. 4 D and E, no increase in proliferation of aged muscle stem cells was detected, as compared to young, and as expected from previous literature, the majority of both young and old satellite cells were quiescent Conboy, I. M., et al.,. Science, 2003. 302(5650): p. 1575-1577; Bischoff, R., Developmental biology, 1986. 115(1): p. 129-139; Conboy, I. M. and T. A. Rando, Dev. Cell, 2002. 3(3): p. 397-409. When added, FGF-2 significantly enhanced the proliferation of quiescent muscle stem cells that were isolated from uninjured muscle (both young and old), as shown in FIGS. 4 D and E, which is consistent with the induction of pERK that is shown in FIG. 4 A, C. However, very interestingly, 90-95% of muscle stem cells derived from uninjured young and old tissue were not proliferating even in the presence of added FGF-2, suggesting that other mitogens and/or cell-fate changes are needed to induce the robust entry of quiescent satellite cells into the cell cycle, also as published (Bischoff, R., J Cell Biol, 1990. 111(1): p. 201-7). These data demonstrate that the localization of FGF-2 within the skeletal muscle compartment changes with age and question whether endogenous FGF-2 is likely to exhaust the pool of aged quiescent satellite cells, since it does not induce significant signaling in these cells.

Example 3

The Pro-regenerative Activity of hESC-Secreted Factors is Contained in Proteins with Heparin Binding Domains To confirm that the factors in hESC conditioned medium were proteins, hESC conditioned Opti-MEM was treated with proteinase-K agarose beads, and the beads were removed before mixing 50/50 with Opti-MEM and 5% mouse serum, for culture with injury-activated satellite cells with associated fibers from old muscle, as above. All proliferative activity of the conditioned medium was lost after proteinase treatment, indicating that protein(s) conferred the pro-regenerative activity (FIG. 7).

To deplete heparin-binding proteins, hESC-conditioned medium was incubated with heparin binding domain-coated acrylic beads. Muscle progenitor cells were then cultured in this heparin-depleted hESC-conditioned medium, hESC-conditioned medium, or controls (medium alone and medium conditioned by differentiated cells that lack the pro-regenerative activity). Proliferation of primary muscle progenitor cells was assayed by BrdU uptake for 2 hours, and cell differentiation was assayed by the expression of eMyHC. Interestingly, hESC-conditioned medium depleted of heparin binding proteins completely lost its pro-regenerative activity on muscle progenitor cells (FIG. 8 A, quantified in B). Even more importantly, the pro-regenerative activity of in the hESC-secreted proteins could be eluted from the heparin-coated beads (FIG. 8 A, quantified in 8B), hence confirming that these factors have heparin-binding domains and suggesting novel strategies for purification of these clinically relevant molecules. Excitingly, when these heparin-binding eluted embryonic proteins were injected at Day 0 and Day 2 into injured muscle (e.g., at the time of the injury and when muscle stem cells become activated for regeneration) old muscle repair became rejuvenated, based on increased formation of de-novo myofibers with centrally located BrdU+ nuclei (FIG. 8C, quantified in 8D). These data reveal the pro-myogenic proteins that are secreted by the hESCs contain heparin-binding domains.

Example 4 hESC-conditioned Opti-MEM has Pro-Survival and Pro-Mitogenic Effects on Neuronal Cell Types To assess the potential positive effect of hESC-secreted proteins on other cell types, specifically neural cells, we cultured rat neural progenitor cells in the presence of hESC-conditioned medium, or in a control medium conditioned by differentiated hESC-derived cells. Specifically, cells were cultured in the 50/50 mix of neural differentiation medium (see Methods) and Opti-MEM, which was conditioned either by the self-renewing hESCs or by the negative control, differentiated hESC-derived cells. The goal was to determine if hESC-secreted factors can enhance proliferation and inhibit differentiation of NPCs, in parallel to our studies demonstrating these embryonic factors enhance muscle precursor proliferation and inhibit their differentiation in a 50/50 mix of fusion medium (Conboy, I. M., H. Yousef, and M. J. Conboy, Aging (Albany NY), 2011. 3(5): p. 555-63). Very interestingly, a significant increase in proliferation of Sox-2+ neural progenitors was observed in cultures exposed to the hESC-produced proteins, an effect that was lost when NPCs were cultured in control medium from differentiated cells (FIG. 6 A, quantified in B). As this effect was similar to what we previously reported for muscle stem/progenitor cells, in that we observe an enhancement of proliferation and inhibition of differentiation of precursor cells by hESC-secreted factors (Conboy, I. M., H. Yousef, and M. J. Conboy, Aging (Albany N.Y.), 2011. 3(5): p. 555-63), it suggests that hESC-secreted proteins enhance the proliferative capacity of progenitor cells in multiple tissue types, and similarly to the situation in muscle, the pro-mitogenic activity is lost when hESCs differentiate.

We next sought to examine whether not only cell proliferation, but cell viability might be enhanced by the hESC-secreted proteins, particularly under pathological conditions. Likewise, we wished to investigate whether the effects of the pro-mitogenic factors would manifest not only on progenitors, but also on terminally differentiated neurons. To answer these questions, we generated human cortical glutamatergic neurons by directed differentiation of embryonic stem cells (see Methods). Specifically, dorsal telencephalic progenitors expressing glutamate and VgluT1 were generated by using Shh and FGF-2. This protocol induced the differentiation of human embryonic stem cells (hESCs) into cultures with up to 74% of neurons expressing glutamate and VgluT1. As an in vitro model of AD, soluble oligomeric forms of Aβ known as "globulomers," which have been implicated in the pathology of Alzheimer's disease (Kuo, Y. M., et al., J Biol Chem, 1996. 271(8): p. 4077-81; Jensen, M., et al., Mol Med, 2000. 6(4): p. 291-302), were added to these cultures of human glutamatergic neurons. They bound Aβ, which led to cell death as measured by the presence of cleaved caspase 3 (FIG. 9C, quantified in 9D).

To examine whether hESC-secreted factors have neuroprotective effects in this in vitro human AD model, Aβ globulomers were added to cortical cultures primarily comprised of glutamatergic neurons in the presence or absence of hESC-conditioned medium. The neurons were pre-incubated with hESC-conditioned Opti-MEM for 1 hr prior to treatment with Aβ globulomers, or alternatively, hESC-conditioned medium was added at 50% to neuron medium, simultaneously with the Aβ globulomers. Analysis with cleaved caspase-3 as an apoptotic marker and MAP2 as neuron marker showed a significant decrease in cell death when neurons were pre-incubated with hESC-secreted factors, as compared to cultures treated with Aβ globulomers alone (FIG. 9C, quantified in 9D). A noticeable but not statistically significant decrease of apoptosis was observed in neuron cultures that were administered with Aβ and hESC-secreted proteins simultaneously (FIG. 9 C, D). These data suggest that hESC-secreted factors exert a protective (anti-apoptotic) effect on human cortical neurons in this AD model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for enhancing proliferation of a muscle cell, the method comprising:
   isolating all heparin binding proteins from a medium conditioned by growth of human embryonic stem cells or human embryonic carcinoma cells, wherein the medium is essentially free of human embryonic stem cells or human embryonic carcinoma cells and wherein the isolating comprises contacting the medium with a solid support conjugated to heparin and eluting the heparin binding proteins bound to the solid support;
   contacting a muscle cell with a composition comprising all of the heparin binding proteins isolated from the medium conditioned by growth of human embryonic stem cells or human embryonic carcinoma cells,
   wherein the contacting is for a period of time sufficient to provide for enhanced proliferation of the muscle cell compared to the absence of the heparin binding proteins.

2. The method of claim 1, wherein the muscle cell is cell of an aged subject.
3. The method of claim 1, wherein the muscle cell is an injured cell.
4. The method of claim 3, wherein the injury is caused by a disease.
5. The method of claim 1, wherein the muscle cell is a diseased cell.
6. The method of claim 1, wherein the muscle cell is a skeletal muscle cell.
7. The method of claim 6, wherein the skeletal muscle cell is a myoblast.
8. The method of claim 1, wherein the muscle cell is an activated satellite cell.
9. The method of claim 1, wherein the heparin binding proteins are isolated from a medium conditioned by growth of human embryonic stem cells.
10. The method of claim 2, wherein the muscle cell is a skeletal muscle cell.
11. The method of claim 10, wherein the skeletal muscle cell is a myoblast.
12. The method of claim 2, wherein the muscle cell is an activated satellite cell.
13. The method of claim 3, wherein the muscle cell is a skeletal muscle cell.

* * * * *